Figure 1:
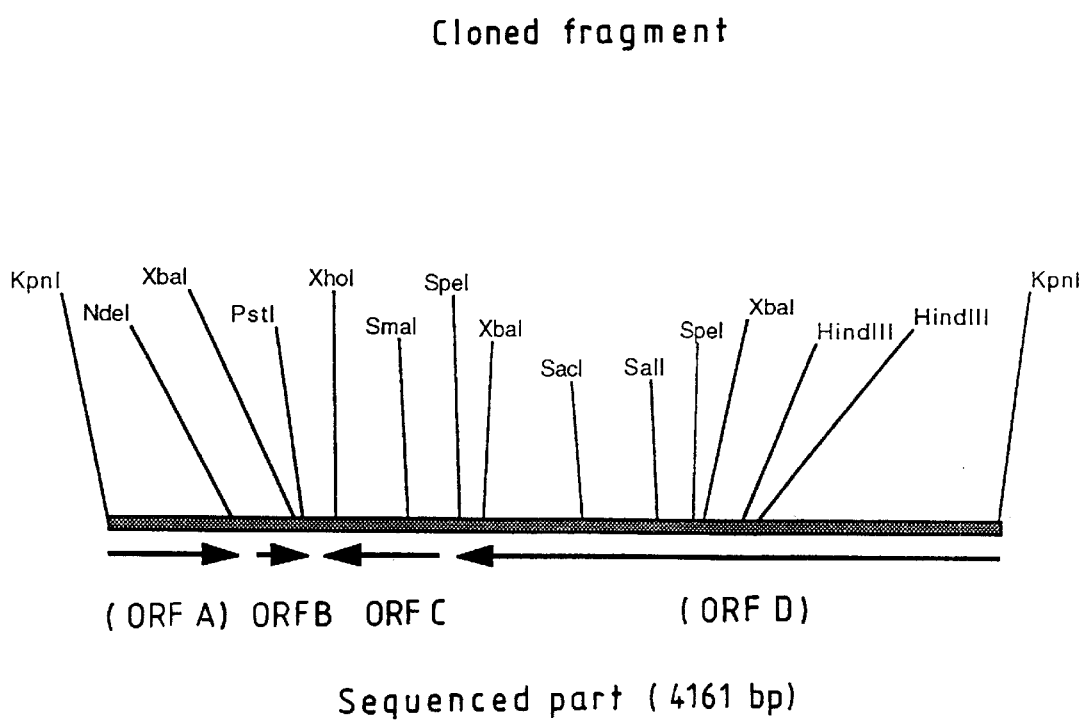

United States Patent [19]

Bublot et al.

[11] Patent Number: 6,033,670
[45] Date of Patent: Mar. 7, 2000

[54] RECOMBINANT LIVE AVIAN VACCINE, USING AS VECTOR THE AVIAN INFECTIOUS LARYNGOTRACHEITIS VIRUS

[75] Inventors: Michel Joseph Marie Bublot, Saint-Genis-Les-Ollieres; Jean-Christophe Francis Audonnet, Lyons; Eliane Louise Francise Laplace, Oullins, all of France

[73] Assignee: Merial, Lyons, France

[21] Appl. No.: 08/790,517

[22] Filed: Jan. 29, 1997

[30] Foreign Application Priority Data

Dec. 16, 1996 [FR] France .................................. 96 15687

[51] Int. Cl.⁷ ............................. A61K 39/00; C12N 7/01; C12N 15/86
[52] U.S. Cl. .................................. 424/199.1; 435/235.1; 435/320.1
[58] Field of Search ................................ 435/320.1, 69.1, 435/235.1; 424/199.1

[56] References Cited

U.S. PATENT DOCUMENTS 5,310,671  5/1994  Binns et al. ......................... 435/235.1

FOREIGN PATENT DOCUMENTS

| | | |
|---|---|---|
| 0 477 056 | 3/1992 | European Pat. Off. . |
| 0 719 864 | 7/1996 | European Pat. Off. . |
| 719864 | 7/1996 | European Pat. Off. ........ C12N 15/86 |
| 2 728 794 | 7/1996 | France . |
| WO 90/02802 | 3/1990 | WIPO . |
| WO 90/02803 | 3/1990 | WIPO . |
| WO 92/03554 | 3/1992 | WIPO . |
| WO 95/08622 | 3/1995 | WIPO . |
| 96/01324 | 1/1996 | WIPO ............................ C12N 15/85 |
| WO 96/00791 | 1/1996 | WIPO . |
| WO 96 21034 | 7/1996 | WIPO . |
| WO 96/29396 | 9/1996 | WIPO . |

OTHER PUBLICATIONS

Chen, et al. (1993) J of Virology, vol. 67 (4) pp. 2142.
Fuchs et al , J. Virol. . Meth. 46:95–105, 1994.
Rixon et al, J. Gen. Virol. . 71:2931–2139, 1990.
Heineman et al, J. Virol. . 69:8109–8223, 1995.
Fuchs et al., Journal of General Virology (1996), 77, 2221–2229.
Kongsuwan et al., Virus Genes 7:3, 297–303, (1993).
Wild et al., Virus Genes 12:2, 107–117, (1996).
Johnson et al., The Journal of Sequencing and Mapping, vol. 5, pp. 191–194.
Johnson et al., Arch. Virol. (1991), 119: 181–198.
Griffin, A.M., Journal of General Virology (1989), 70, 3085–3089.
Griffin, A.M., Journal of General Virology (1991), 72, 393–398.
Griffin, A.M., Nucleic Acids Research, vol. 18, No. 12. p. 3664 (1990).
Griffin et al., Journal of General Virology (1990), 71:841–850.
Keeler et al., Avian Diseases, 35:920–929, (1991).
Kongsuwan et al., Virology, 184, 404–410, (1991).
Poulsen et al., Virus Genes, 5:4, 335–347, (1991).
Kingsley et al., Virology, 203, 336–343, (1994).
Johnson et al., Arch Virol. (1995), 140: 623–634.
Johnson et al., Virus Research, 35 (1995), 193–204.
Kongsuwan et al., Arch. Virol. (1995), 140: 27–39.
Kongsuwan et al., Virus Research, 29 (1993), 125–140.
Fuchs et al. *Journal of General Virology* (1996), vol. 77, pp. 2221–2229.

*Primary Examiner*—Mary E. Mosher
*Attorney, Agent, or Firm*—Frommer Lawrence & Haug LLP; William S. Frommer; Thomas J. Kowalski

[57] ABSTRACT

The recombinant live avian vaccine comprises as vector an ILTV virus comprising and expressing at least one heterologous nucleotide sequence, this nucleotide sequence being inserted into the insertion locus formed by the intergenic region located between the stop codons of ORF B and ORF C of ILTV, which region, in a particular strain of ILTV, is defined between nucleotides 908 and 994 in SEQ ID NO:1.

38 Claims, 27 Drawing Sheets

KpnI
COL A

```
   1 GGTACCGAGATCCCCTCTGTGACAGAAGTTCTATATGGAGCCTCGTCTATTGACTGTGTT
   1▶ GlyThrGluIleProSerValThrGluValLeuTyrGlyAlaSerSerIleAspCysVal
  61 TCCGGATCGTACGAATGTCATGATACGCATTCTCATGTTACTCCGGACCACGCAAAAGAC
  21▶ SerGlySerTyrGluCysHisAspThrHisSerHisValThrProAspHisAlaLysAsp
 121 GTAGCCGTCCAAGGGCATGTCAAAACGAATAACACCGAAGATGTAGAATCTTTGGACTCG
  41▶ ValAlaValGlnGlyHisValLysThrAsnAsnThrGluAspValGluSerLeuAspSer
 181 TGTGGCTTTGACAGTGTTTTCATGATATTTTCATTCGGGGAACTCGGGAGAAGACAGCTT
  61▶ CysGlyPheAspSerValPheMetIlePheSerPheGlyGluLeuGlyArgArgGlnLeu
 241 ACCGATAACATTCGAAAAGACATTTGTACTTCCCTAGACAGAGTTCCGATGGCATGTACT
  81▶ ThrAspAsnIleArgLysAspIleCysThrSerLeuAspArgValProMetAlaCysThr
 301 AAGACGTCCGCATTTGCAGGTGCAAATAGACATCAGAAAAGTTTGCAGATGTTTCTCTTT
 101▶ LysThrSerAlaPheAlaGlyAlaAsnArgHisGlnLysSerLeuGlnMetPheLeuPhe
 361 TGCAAGAGAAGACATGCCCCGCAAATAAGGGCTCGCCTAAAAGACATTATTTCGTCAAGA
 121▶ CysLysArgArgHisAlaProGlnIleArgAlaArgLeuLysAspIleIleSerSerArg
 421 AAGTCAAGAAAATATTTTACGCAGTCCGAGGATGGAGAAACTCACCCCGGTGTGCCAGTT
 141▶ LysSerArgLysTyrPheThrGlnSerGluAspGlyGluThrHisProGlyValProVal
 481 TTCTTTCACGAGTTTGTAGCCCATGCCCCGGTATTTATTCCACGCGACAATCTTGCCCAT
 161▶ PhePheHisGluPheValAlaHisAlaProValPheIleProArgAspAsnLeuAlaHis
```

NdeI

```
 541 GCCTGTCGCAGATTGGCCAGGCATATGACTGGAGGAATGGCGTGTTGACTTACGTGGGCG
 181▶ AlaCysArgArgLeuAlaArgHisMetThrGlyGlyMetAlaCys•••
 601 CGCCTCTGGGTGGAACCCAGCGCTAGAACATTTATACCTGCCCCATTGCGAAAGTTACTC
```

COL B

```
 661 AGAACGCGAATATTGCACTTCCTGGACTATGAAGTACGGTCAGGCTGCTATTGCAACTGA
                                  1▶ MetLysTyrGlyGlnAlaAlaIleAlaThrAs
 721 TATGGACTTTGCCCGCATGTCTCGCCAGCCTCCACGGAAGAACTCCAGGTGCTCTTCGGC
  11▶ pMetAspPheAlaArgMetSerArgGlnProProArgLysAsnSerArgCysSerSerAl
 781 ACGGACGGCTGCGTTACAGGGTAATGGATATTGCTTTCTACCGAAGTCGGAAAAGTTGCC
  31▶ aArgThrAlaAlaLeuGlnGlyAsnGlyTyrCysPheLeuProLysSerGluLysLeuPr
```

XbaI                                                          PstI

```
 841 TGAGCTACCCTCTAGACATTTCGAGACCCGATTTTCCTCACTACTACCTCCAGCTGCAGC
  51▶ oGluLeuProSerArgHisPheGluThrArgPheSerSerLeuLeuProProAlaAlaAl
 901 TAAGTGACAGCAACTATGAAGGTCAACTCATTTCCGCAATGCGACGCAATAATTAAATGC
  71▶ aLys•••
 961 TCGTATTTCATAATTTGGTGTTTATTACTTTTATTTATTCCTCTAACAGTCCGGCATGCC
                                                          179◀ •••GluGluLeuLeuGlyAlaHisAr
```

XhoI

```
1021 TTGCCGCAAACTCTACAAGATCTCGAGGAACGCTTTCCTCTGGACACTCCAGCGATTCTG
 170◀ gAlaAlaPheGluValLeuAspArgProValSerGluGluProCysGluLeuSerGluPr
1081 GAGAGGATTGGGAACATGTGGGGTGGTGTGCGCGCTAGATGCTAGATCTTCCGGGGTTT
 150◀ oSerSerGlnSerCysThrProThrThrHisAlaSerSerAlaLeuAspGluProThrGl
1141 CGTATATGGTTACAGTTAAGTGAGCGACGCCCAAAAAATTCATCATGGTGATGTTGCCGC
 130◀ uTyrIleThrValThrLeuHisAlaValGlyLeuPheAsnMetMetThrIleAsnGlySe
1201 TGCTCCACCGTTCTCGCGTTCCTCCGCGCCCTAGAAACCAACATGCCGAGAACTGAAAAG
 110◀ rSerTrpArgGluArgThrGlyGlyArgGlyLeuPheTrpCysAlaSerPheGlnPheAl
1261 CTAATGTTTCTCCTGAGGGTCCTCGGTGAGAACCATTGCGCTCCAAACAGTATGCGCAAA
  90◀ aLeuThrGluGlySerProGlyArgHisSerGlyAsnArgGluLeuCysTyrAlaCysPh
1321 ATTCTTCTTCACAGTCTACAGCGATCATTGTTGCGACGGGATTGTGAATTACTATTACTT
  70◀ eGluGluGluCysAspValAlaIleMetThrAlaValProAsnHisIleValIleValLy
```

FIG.2 ..

```
       SmaI
1381   TCCCGGGTGGTAATTGGTGGCGATACATTTTATTTCCGATGCAAATAAACCGCATTCCTC
   50◄ sGlyProProLeuGlnHisArgTyrMetLysAsnGlyIleCysIlePheArgMetGlyGl
1441   CATCGCATGAGTATACTACTTGTTCGTATTCGGTGGCCGAGCCATGCCCCAAGCCTTGGA
   30◄ yAspCysSerTyrValValGlnGluTyrGluThrAlaSerGlyHisGlyLeuGlyGlnVa
                                    COL C
1501   CTCCTACCATTACGTAGCTTATGAAAATCATGTTCTCGGGACGAGGAGGGTATGCAACAC
   10◄ lGlyValMetValTyrSerIlePheIleMet
1561   TCCAAACGACGGTGGGAAACTGATTTTAAAGCCACGCGTGTGGCTACTTTTGAGGATTAG
                                                              848◄•••T
       SpeI
1621   TATACTAGTCGCGTTTCTTTGCATCTGAGCGCGCGAAGAATGTGTTGGCTTACTTGTCGA
  846◄ yrValLeuArgThrGluLysCysArgLeuAlaArgLeuIleHisGlnSerValGlnArgT
1681   GTATCTTCGTATTTCGTTCGCAGGGGGTTTAAGTTCATGCGCAAATATTCGCTACTCGTT
  826◄ hrAspGluTyrLysThrArgLeuProAsnLeuAsnMetArgLeuTyrGluSerSerThrV
       XbaI
1741   ACTCTAGACATTGCTACGTATGCAGTATTTAATTTCATTGTTCCGTGAGAAAAACATATT
  806◄ alArgSerMetAlaValTyrAlaThrAsnLeuLysMetThrGlyHisSerPheCysIleA
1801   GCTACCCTGTCTAAACTTAACCCTTGAGATCGTGTGATCGTCATTGCAAGGCTCGAACTT
  786◄ laValArgAspLeuSerLeuGlyGlnSerArgThrIleThrMetAlaLeuSerSerSerI
1861   ATTCCGTGGTCAATTGTTATGGCCATCCTTAATTCCTGTCCACCTATATTATCGACAAAA
  766◄ leGlyHisAspIleThrIleAlaMetArgLeuGluGlnGlyGlyIleAsnAspValPheT
1921   GTTGCTTTGTTATGGCACAGGACTGAAACGAACCCCATTTGATCCCTTACGACAAGTCTT
  746◄ hrAlaLysAsnHisCysLeuValSerValPheGlyMetGlnAspArgValValLeuArgP
1981   GGCAAGTCTAGCATTTGTAAAATTGGCTCGGCCCATTCGTGGGCTTTTGAGGTGTCCTCA
  726◄ roLeuAspLeuMetGlnLeuIleProGluAlaTrpGluHisAlaLysSerThrAspGluA
2041   GCATATCCCGGAAATCTTGCTCGCGTAATCCCGCGTAAGGTATATGTGTCGGTTTGAGCA
  706◄ laTyrGlyProPheArgAlaArgThrIleGlyArgLeuThrTyrThrAspThrGlnAlaA
2101   GCAAATGCACATACTGCTCCCTTGAAACTGGAGATAGAAATTTCTTGACTTGAGAAAGAA
  686◄ laPheAlaCysValAlaGlyLysPheSerSerIleSerIleGluGlnSerSerPheSerA
```

.. FIG. 2 ..

```
                                                                    SacI
2161 GCCGTTCCGACGAATGAGCTAAAGGGGGCGGCAGTAAATACACTCCCAAAGAGCTCACAC
 666◀ laThrGlyValPheSerSerPheProAlaAlaThrPheValSerGlyPheLeuGluCysL
2221 AGCACCGCGTAACGTAAAGTATAAATTCTTTTCATCTGCTCGAAATAACTAAATATTTCT
 646◀ euValAlaTyrArgLeuThrTyrIleArgLysMetGlnGluPheTyrSerPheIleGluG
2281 TGACCGTGGACATCGCTCCCGCAAATCTCATAATTTAGATAGAATTGATCTAACGACTTA
 626◀ lnGlyHisValAspSerGlyCysIleGluTyrAsnLeuTyrPheGlnAspLeuSerLysA
2341 TCAAAAATATCGAATAAATCATCTTTGTCATTCACATCGGCATTCGGACATTCATCTTCG
 606◀ spPheIleAspPheLeuAspAspLysAspAsnValAspAlaAsnProCysGluAspGluA
2401 TTAAAACAAAATTTTTCACCATTTCCCATGTCAAAGTTCTGAGTTTCTGGCTCCGGCATT
 586◀ snPheCysPheLysGluGlyAsnGlyMetAspPheAsnGlnThrGluProGluProMetA
2461 GCTAGGGAGTACAACCTGTCATACGCCATTGTTAATTTATCTTCGGGGAGGCCCTCTGTT
 566◀ laLeuSerTyrLeuArgAspTyrAlaMetThrLeuLysAspGluProLeuGlyGluThrA
                                                  SalI
2521 CGGAGAAATTCGTAAAATTTAATCATCCCATAGTATAGCAAGGTCGACAGAAAGTGATAG
 546◀ rgLeuPheGluTyrPheLysIleMetGlyTyrTyrLeuLeuThrSerLeuPheHisTyrA
2581 GCAAATTCTACTTTGTCTTCTCCATACGTCTTGAGAAAGCTATCTTCGGATAATACATGT
 526◀ laPheGluValLysAspGluGlyTyrThrLysLeuPheSerAspGluSerLeuValHisA
2641 GCGAATTTTTCAAATGTTCCCTCAAAACCGAAGATCAATTTTTTTACCTTTTTTGTTACC
 506◀ laPheLysGluPheThrGlyGluPheGlyPheIleLeuLysLysValLysLysThrValT
                                        SpeI
2701 GTGATCTGGCTATTGAGTACGTGCGAGGCATCAGTCGTTACTAGTGTATATTCATTACTC
 486◀ hrIleGlnSerAsnLeuValHisSerAlaAspThrThrValLeuThrTyrGluAsnSerG
                                        XbaI
2761 TCATCTCGATGGTATTCAAATCTGGGCGCGGTCACATCTAGATCCCTGCTCTGTGAATAG
 466◀ luAspArgHisTyrGluPheArgProAlaThrValAspLeuAspArgSerGlnSerTyrA
2821 TTTCCAAGGCGAGAGGAATTGTTTTGCAGCCAGCGATCAATATTTAGTGTCTCTTGACCC
 446◀ snGlyLeuArgSerSerAsnAsnGlnLeuTrpArgAspIleAsnLeuThrGluGlnGlyT
```

..FIG. 2..

```
2881 GTCAGGGATTTATACTTTTCAAATGCCGCCATATCTACTATTGTATACATCGGCAGGAGA
 426◀ hrLeuSerLysTyrLysGluPheAlaAlaMetAspValIleThrTyrMetProLeuLeuP
                                                    HindIII
2941 AATACCCTATATTTTTCAGATTTCTGTGCACGAAGCTTTGCGTGCAATTTAGAAACGTAT
 406◀ heValArgTyrLysGluSerLysGlnAlaArgLeuLysAlaHisLeuLysSerValTyrG
                                     HindIII
3001 TCTTTAACTTCTTCGTGGGACGAGAAAAGCCTAGTCCATCCAGGAAGCTTTGATGGATCT
 386◀ luLysValGluGluHisSerSerPheLeuArgThrTrpGlyProLeuLysSerProAspL
3061 TTGATGAATGATTCTGATACAATGAACTGATCTAAGAATCTGGCATGGCGTTTTGTCAAA
 366◀ ysIlePheSerGluSerValIlePheGlnAspLeuPheArgAlaHisArgLysThrLeuP
3121 GGTAACCCAAATTCAAATGCCTTTAATACTTCTCCGAAAGCAGGCTCCGAGCATCGTTTA
 346◀ roLeuGlyPheGluPheAlaLysLeuValGluGlyPheAlaProGluSerCysArgLysA
3181 TTATTAATAAAGATGGCCCACTGCTTCTTGATATTCAGGACTGAAAACAGTGTAGGAGTA
 326◀ snAsnIlePheIleAlaTrpGlnLysLysIleAsnLeuValSerPheLeuThrProThrC
3241 CAAATAAGATTACTTAAAATGTTTATGCTGCTGGATATAAGGTGTCGTTGATTTCTGTGC
 306◀ ysIleLeuAsnSerLeuIleAsnIleSerSerSerIleLeuHisArgGlnAsnArgHisG
3301 TCGAAGCTGCTTTCCATTGCGTCTGTCTGTAGGGGAGCCAATGCACACGATCACTGGC
 286◀ luPheSerSerGluMetAlaAspThrGlnThrProSerGlyIleCysValIleValProL
3361 TTCTTCCCGTCCTGATACATAGGCGTTTTCCACAATGCATTCATGAGCCACCACGAATAT
 266◀ ysLysGlyAspGlnTyrMetProThrLysTrpLeuAlaAsnMetLeuTrpTrpSerTyrV
3421 ACTATTGCAGTCAATATATGTTTCCCTAAAACTCCAGCCTCATCAACAAGGATAATGTTG
 246◀ alIleAlaThrLeuIleHisLysGlyLeuValGlyAlaGluAspValLeuIleIleAsnS
3481 CTTTTGACAAATGGAGGCATAGAGGAAATTAGGAAAGGTGCAAGGTTTACAAATTTGCGT
 226◀ erLysValPheProProMetSerSerIleLeuPheProAlaLeuAsnValPheLysArgS
3541 GAAGTTTTCTGCTGGAGTGTTTGAAGGACAGACAAAGCTACCGGAGATGCCGTGTCATG
 206◀ erThrLysGlnGlnLeuThrGlnLeuValSerLeuAlaValProSerAlaThrAspIleA
3601 GCGCGTGCAGTAATGTCCTTTATCACGTCCCAATAATAATAAATGTCGGCCATTTGATGT
 186◀ laArgAlaThrIleAspLysIleValAspTrpTyrTyrTyrIleAspAlaMetGlnHisG
3661 TCTGCCAACGAACGTTGTTCGTGAGGTTTTTCAAACTTGAATCGTCCTAGCACAGCCTGT
 166◀ luAlaLeuSerArgGlnGluHisProLysGluPheLysPheArgGlyLeuValAlaGlnV
3721 ACGTTGTTTCCTTTGAAGCCAAAGTTTTGAAAAATAGTATGAATGGGACAAGAGGTGTAA
 146◀ alAsnAsnGlyLysPheGlyPheAsnGlnPheIleThrHisIleProCysSerThrTyrS
3781 GAGGCAGATAGCTTATTGAAGATATTAAGAGCAGCTATGCGCGTTGAGCCAGTAACGATG
 126◀ erAlaSerLeuLysAsnPheIleAsnLeuAlaAlaIleArgThrSerGlyThrValIleC
3841 CAATTCAATGTTTCATTAAGAGTTTGAATGCAAGTACTTTTTCCTGAGCCGGCGTTACCG
 106◀ ysAsnLeuThrGluAsnLeuThrGlnIleCysThrSerLysGlySerGlyAlaAsnGlyT
3901 GTGATTAGATAAACATTAAATGGTAATTCCGCCAGAGGCAAAGTGGTCGGTTCATCTAAA
  86◀ hrIleLeuTyrValAsnPheProLeuGluAlaLeuProLeuThrThrProGluAspLeuA
3961 CGTGCCACAGTCTCAAACCAAGACAGTTGCGGCTTGGAGTCTTCATGAACAGCTTGTTCT
  66◀ rgAlaValThrGluPheTrpSerLeuGlnProLysSerAspGluHisValAlaGlnGluS
4021 GATAGGATTGTAATGTCCGATAAAATCGCCTGAATGCTCTGCATTGCCGAAAAATTTAAG
  46◀ erLeuIleThrIleAspSerLeuIleAlaGlnIleSerGlnMetAlaSerPheAsnLeuT
4081 TAAACAGGAGTGGTGATTTCTATTTCCCGCCTGCTCTTCCCGAAAATGGACATGCCATT
  26◀ yrValProThrThrIleGluIleGluArgArgSerLysGlySerPheProCysAlaMetL
          KpnI
          COL D
4141 TTCCCAATTGCGTCAGGTACC
   6◀ ysGlyIleAlaAspProVal
```

.. FIG. 2

```
   1 TGCTACCTGATGTACAAGCAAAAGGCACAACAAAAGACCTTGTTATGGCTTGGGAATAAT
  61 ACCCTTGATCAGATGAGAGCCACTACAAAAATATGAATACAAACGAGAGGCGGAGGTATC
 121 CCCAATAGCAATTTGCGTGTAAATTCTGGCAACCTGTTAATTAGAAGAATTAAGAAAAAA
 181 CCACTGGATGTAAGTGACAAACAAGCAATACACGGGTAGAACGGTCGGAGAAGCCACCCC
 241 TCAATCGGGAATCAGGCCTCACAACGTCCTTTCTACCGCATCATCAATAGCAGACTTCGG
 301 TCATGGACCGTGCAGTTAGCAGAGTTGCGCTAGAGAATGAAGAAAGAGAAGCAAAGAATA
   1▶MetAspArgAlaValSerArgValAlaLeuGluAsnGluGluArgGluAlaLysAsnT
 361 CATGGCGCTTTGTATTCCGGATTGCAATCTTACTTTTAATAGTAACAACCTTAGCCATCT
  20▶hrTrpArgPheValPheArgIleAlaIleLeuLeuLeuIleValThrThrLeuAlaIleS
 421 CTGCAACCGCCCTGGTATATAGCATGGAGGCTAGCACGCCTGGCGACCTTGTTGGCATAC
  40▶erAlaThrAlaLeuValTyrSerMetGluAlaSerThrProGlyAspLeuValGlyIleP
 481 CGACTATGATCTCTAAGGCAGAAGAAAAGATTACATCTGCACTCAGTTCTAATCAAGATG
  60▶roThrMetIleSerLysAlaGluGluLysIleThrSerAlaLeuSerSerAsnGlnAspV
 541 TAGTAGATAGGATATATAAGCAGGTGGCCCTTGAGTCTCCATTGGCGTTGCTAAACACTG
  80▶alValAspArgIleTyrLysGlnValAlaLeuGluSerProLeuAlaLeuLeuAsnThrG
 601 AATCTGTAATTATGAATGCAATAACGTCTCTCTCTTATCAAATCAATGGAGCTGCAAATA
 100▶luSerValIleMetAsnAlaIleThrSerLeuSerTyrGlnIleAsnGlyAlaAlaAsnA
                                                              BspHI
 661 ATAGCGGGTGTGGGGCACCTGTTCATGACCCAGATTATATCGGGGGGATAGGCAAAGAAC
 120▶snSerGlyCysGlyAlaProValHisAspProAspTyrIleGlyGlyIleGlyLysGluL
 721 TTATTGTGGATGACGCTAGTGATGTCACATCATTCTATCCCTCTGCGTTCCAAGAACACC
 140▶euIleValAspAspAlaSerAspValThrSerPheTyrProSerAlaPheGlnGluHisL
 781 TGAACTTTATCCCGGCACCTACTACAGGATCAGGTTGCACTCGGATACCCTCATTCGACA
 160▶euAsnPheIleProAlaProThrThrGlySerGlyCysThrArgIleProSerPheAspI
 841 TAAGCGCTACCCACTACTGTTACACTCACAATGTGATATTATCTGGTTGCAGAGATCACT
 180▶leSerAlaThrHisTyrCysTyrThrHisAsnValIleLeuSerGlyCysArgAspHisS
 901 CACACTCATATCAGTACTTAGCACTTGGCGTGCTTCGGACATCTGCAACAGGGAGGGTAT
 200▶erHisSerTyrGlnTyrLeuAlaLeuGlyValLeuArgThrSerAlaThrGlyArgValP
 961 TCTTTTCTACTCTGCGTTCCATCAATTTGGATGACAGCCAAAATCGGAAGTCTTGCAGTG
 220▶hePheSerThrLeuArgSerIleAsnLeuAspAspSerGlnAsnArgLysSerCysSerV
1021 TGAGTGCAACTCCCTTAGGTTGTGATATGCTGTGCTCTAAAATCACAGAGACTGAGGAAG
 240▶alSerAlaThrProLeuGlyCysAspMetLeuCysSerLysIleThrGluThrGluGluG
                                                          ClaI
1081 AGGATTATAGTTCAATTACGCCTACATCGATGGTGCACGGAAGGTTAGGGTTTGACGGTC
 260▶luAspTyrSerSerIleThrProThrSerMetValHisGlyArgLeuGlyPheAspGlyG
1141 AATACCATGAGAAGGACTTAGACGTCATAACTTTATTTAAGGATTGGGTGGCAAATTACC
 280▶lnTyrHisGluLysAspLeuAspValIleThrLeuPheLysAspTrpValAlaAsnTyrP
1201 CAGGAGTGGGGGGTGGGTCTTTTATTAACAACCGCGTATGGTTCCCAGTCTACGGAGGGC
 300▶roGlyValGlyGlyGlySerPheIleAsnAsnArgValTrpPheProValTyrGlyGlyL
1261 TAAAACCCAATTCGCCTAGTGACACCGCACAAGAAGGGAGATATGTAATATACAAGCGCT
 320▶euLysProAsnSerProSerAspThrAlaGlnGluGlyArgTyrValIleTyrLysArgT
1321 ACAATGACACATGCCCAGATGAACAAGATTACCAGATTCGGATGGCTAAGTCTTCATATA
 340▶yrAsnAspThrCysProAspGluGlnAspTyrGlnIleArgMetAlaLysSerSerTyrL
1381 AGCCTGGGCGGTTTGGTGGAAAACGCGTACAGCAGGCCATCTTATCTATCAAGGTGTCAA
 360▶ysProGlyArgPheGlyGlyLysArgValGlnGlnAlaIleLeuSerIleLysValSerT
1441 CATCTTTGGGCGAGGACCCGGTGCTGACTGTACCGCCAATACAATCACACTCATGGGGG
 380▶hrSerLeuGlyGluAspProValLeuThrValProProAsnThrIleThrLeuMetGlyA
1501 CCGAACGGAGAGTTCTCACAGTAGGGACATCTCATTTCTTGTACCAGCGAGGGTCTTCAT
 400▶laGluArgArgValLeuThrValGlyThrSerHisPheLeuTyrGlnArgGlySerSerT
```

FIG.10..

```
1561 ACTTCTCTCCTGCTTTATTATACCCTATGACAGTCAACAACAAAACGGCTACTCTTCATA
 420▶ yrPheSerProAlaLeuLeuTyrProMetThrValAsnAsnLysThrAlaThrLeuHisS
1621 GTCCTTACACATTCAATGCTTTCACTAGGCCAGGTAGTGTCCCTTGTCAGGCATCAGCAA
 440▶ erProTyrThrPheAsnAlaPheThrArgProGlySerValProCysGlnAlaSerAlaA
1681 GATGCCCCAACTCATGTGTCACTGGAGTTTATACTGATCCGTATCCCTTAGTCTTCCATA
 460▶ rgCysProAsnSerCysValThrGlyValTyrThrAspProTyrProLeuValPheHisA
1741 GGAACCATACCTTGCGGGGGGTATTCGGGACAATGCTTGATGATGAACAAGCAAGACTTA
 480▶ rgAsnHisThrLeuArgGlyValPheGlyThrMetLeuAspAspGluGlnAlaArgLeuA
                       PstI
1801 ACCCTGTATCTGCAGTATTTGATAACATATCCCGCAGTCGCATAACCCGGGTAAGTTCAA
 500▶ snProValSerAlaValPheAspAsnIleSerArgSerArgIleThrArgValSerSerS
1861 GCCGTACTAAGGCAGCATACACGACATCGACATGTTTTAAAGTTGTCAAGACCAATAAAA
 520▶ erArgThrLysAlaAlaTyrThrThrSerThrCysPheLysValValLysThrAsnLysT
1921 CATATTGCCTCAGCATTGCAGAAATATCCAATACCCTCTTCGGGGAATTCAGGATCGTTC
 540▶ hrTyrCysLeuSerIleAlaGluIleSerAsnThrLeuPheGlyGluPheArgIleValP
1981 CTTTACTAGTTGAGATTCTCAAGGATGATGGGATTTAAGAAGCCAGGTCTGGCCAGTTGA
 560▶ roLeuLeuValGluIleLeuLysAsp
2041 GTCAACTGCGAGAGGGTCGGAAAGATGACATTGTGTCACCTTTTTTTTGTAATGCCAAGG
2101 ATCAAACTGGATACCGGCGCGAGCCCGAATCCTATGCTGCCAGTCAGCCATAATCAGATA
2161 GTACTAATATGATTAGTCTTAATCTTGTCGATAGTAACTTGGTTAAGAAAAAATATGAGT
2221 GGTAGTGAGATACACAGCTAAACAACTCACGAGAGATAGCACGGGTAGGACATGGCGAGC
2281 TCCGGTCCCGAAAGGGCAGAGCATCAGATTATCCTACCAGAGTCACATCTGTCCTCACCA
2341 TTGGTCAAGCACAAACTGCTCTATTACTGGAAATTAACTGGCGTACCGCTTCCTGACGAA
2401 TGTGACTTCGACCACCTCATTATCAGCCGACAATGGAAGAAAATACTTGAATCGGCCACT
2461 CCTGACACTGAGAGGATGATAAAGCTCGGGCGGGCAGTACACCAGACTCTCGACCACCGC
2521 C
```

.. FIG.10

UL3

```
   1 GGTACCGAGATCCCCTCTGTGACAGAAGTTCTATATGGAGCCTCGTCTATTGACTGTGTT
   1▶ GlyThrGluIleProSerValThrGluValLeuTyrGlyAlaSerSerIleAspCysVal
  61 TCCGGATCGTACGAATGTCATGATACGCATTCTCATGTTACTCCGGACCACGCAAAAGAC
  21▶ SerGlySerTyrGluCysHisAspThrHisSerHisValThrProAspHisAlaLysAsp
 121 GTAGCCGTCCAAGGGCATGTCAAAACGAATAACACCGAAGATGTAGAATCTTTGGACTCG
  41▶ ValAlaValGlnGlyHisValLysThrAsnAsnThrGluAspValGluSerLeuAspSer
 181 TGTGGCTTTGACAGTGTTTTCATGATATTTTCATTCGGGGAACTCGGGAGAAGACAGCTT
  61▶ CysGlyPheAspSerValPheMetIlePheSerPheGlyGluLeuGlyArgArgGlnLeu
 241 ACCGATAACATTCGAAAAGACATTTGTACTTCCCTAGACAGAGTTCCGATGGCATGTACT
  81▶ ThrAspAsnIleArgLysAspIleCysThrSerLeuAspArgValProMetAlaCysThr
 301 AAGACGTCCGCATTTGCAGGTGCAAATAGACATCAGAAAAGTTTGCAGATGTTTCTCTTT
 101▶ LysThrSerAlaPheAlaGlyAlaAsnArgHisGlnLysSerLeuGlnMetPheLeuPhe
 361 TGCAAGAGAAGACATGCCCCGCAAATAAGGGCTCGCCTAAAAGACATTATTTCGTCAAGA
 121▶ CysLysArgArgHisAlaProGlnIleArgAlaArgLeuLysAspIleIleSerSerArg
 421 AAGTCAAGAAAATATTTTACGCAGTCCGAGGATGGAGAAACTCACCCCGGTGTGCCAGTT
 141▶ LysSerArgLysTyrPheThrGlnSerGluAspGlyGluThrHisProGlyValProVal
 481 TTCTTTCACGAGTTTGTAGCCCATGCCCCGGTATTTATTCCACGCGACAATCTTGCCCAT
 161▶ PhePheHisGluPheValAlaHisAlaProValPheIleProArgAspAsnLeuAlaHis
 541 GCCTGTCGCAGATTGGCCAGGCATATGACTGGAGGAATGGCGTGTTGACTTACGTGGGCG
 181▶ AlaCysArgArgLeuAlaArgHisMetThrGlyGlyMetAlaCys•••
 601 CGCCTCTGGGTGGAACCCAGCGCTAGAACATTTATACCTGCCCCATTGCGAAAGTTACTC
```

UL3.5

```
 661 AGAACGCGAATATTGCACTTCCTGGACTATGAAGTACGGTCAGGCTGCTATTGCAACTGA
   1▶                                  MetLysTyrGlyGlnAlaAlaIleAlaThrAs
 721 TATGGACTTTGCCCGCATGTCTCGCCAGCCTCCACGGAAGAACTCCAGGTGCTCTTCGGC
  11▶ pMetAspPheAlaArgMetSerArgGlnProProArgLysAsnSerArgCysSerSerAl
 781 ACGGACGGCTGCGTTACAGGGTAATGGATATTGCTTTCTACCGAAGTCGGAAAAGTTGCC
  31▶ aArgThrAlaAlaLeuGlnGlyAsnGlyTyrCysPheLeuProLysSerGluLysLeuPr
 841 TGAGCTACCCTCTAGACATTTCGAGACCCGATTTTCCTCACTACTACCTCCAGCTGCAGC
  51▶ oGluLeuProSerArgHisPheGluThrArgPheSerSerLeuLeuProProAlaAlaAl
 901 TAAGTGACAGCAACTATGAAGGTCAACTCATTTCCGCAATGCGACGCAATAATTAAATGC
  71▶ aLys•••
 961 TCGTATTTCATAATTTGGTGTTTATTACTTTTATTTATTCCTCTAACAGTCCGGCATGCC
                                         179◀ •••GluGluLeuLeuGlyAlaHisAr
1021 TTGCCGCAAACTCTACAAGATCTCGAGGAACGCTTTCCTCTGGACACTCCAGCGATTCTG
 170◀ gAlaAlaPheGluValLeuAspArgProValSerGluGluProCysGluLeuSerGluPr
1081 GAGAGGATTGGGAACATGTGGGGGTGGTGTGCGCGCTAGATGCTAGATCTTCCGGGGTTT
 150◀ oSerSerGlnSerCysThrProThrThrHisAlaSerSerAlaLeuAspGluProThrGl
1141 CGTATATGGTTACAGTTAAGTGAGCGACGCCCAAAAAATTCATCATGGTGATGTTGCCGC
 130◀ uTyrIleThrValThrLeuHisAlaValGlyLeuPheAsnMetMetThrIleAsnGlySe
1201 TGCTCCACCGTTCTCGCGTTCCTCCGCGCCCTAGAAACCAACATGCCGAGAACTGAAAAG
 110◀ rSerTrpArgGluArgThrGlyGlyArgGlyLeuPheTrpCysAlaSerPheGlnPheAl
1261 CTAATGTTTCTCCTGAGGGTCCTCGGTGAGAACCATTGCGCTCCAAACAGTATGCGCAAA
  90◀ aLeuThrGluGlySerProGlyArgHisSerGlyAsnArgGluLeuCysTyrAlaCysPh
1321 ATTCTTCTTCACAGTCTACAGCGATCATTGTTGCGACGGGATTGTGAATTACTATTACTT
  70◀ eGluGluGluCysAspValAlaIleMetThrAlaValProAsnHisIleValIleValLy
```

FIG. 18..

```
1381 TCCCGGGTGGTAATTGGTGGCGATACATTTTATTTCCGATGCAAATAAACCGCATTCCTC
  50◄ sGlyProProLeuGlnHisArgTyrMetLysAsnGlyIleCysIlePheArgMetGlyGl
1441 CATCGCATGAGTATACTACTTGTTCGTATTCGGTGGCCGAGCCATGCCCCAAGCCTTGGA
  30◄ yAspCysSerTyrValValGlnGluTyrGluThrAlaSerGlyHisGlyLeuGlyGlnVa
                                UL4
1501 CTCCTACCATTACGTAGCTTATGAAAATCATGTTCTCGGGACGAGGAGGGTATGCAACAC
  10◄ lGlyValMetValTyrSerIlePheIleMet
1561 TCCAAACGACGGTGGGAAACTGATTTTAAAGCCACGCGTGTGGCTACTTTTGAGGATTAG
                                                          841◄···T
1621 TATACTAGTCGCGTTTCTTTGCATCTGAGCGCGCGAAGAATGTGTTGGCTTACTTGTCGA
 839◄ yrValLeuArgThrGluLysCysArgLeuAlaArgLeuIleHisGlnSerValGlnArgT
1681 GTATCTTCGTATTTCGTTCGCAGGGGGTTTAAGTTCATGCGCAAATATTCGCTACTCGTT
 819◄ hrAspGluTyrLysThrArgLeuProAsnLeuAsnMetArgLeuTyrGluSerSerThrV
1741 ACTCTAGACATTGCTACGTATGCAGTATTTAATTTCATTGTTCCGTGAGAAAAACATATT
 799◄ alArgSerMetAlaValTyrAlaThrAsnLeuLysMetThrGlyHisSerPheCysIleA
1801 GCTACCCTGTCTAAACTTAACCCTTGAGATCGTGTGATCGTCATTGCAAGGCTCGAACTT
 779◄ laValArgAspLeuSerLeuGlyGlnSerArgThrIleThrMetAlaLeuSerSerSerI
1861 ATTCCGTGGTCAATTGTTATGGCCATCCTTAATTCCTGTCCACCTATATTATCGACAAAA
 759◄ leGlyHisAspIleThrIleAlaMetArgLeuGluGlnGlyGlyIleAsnAspValPheT
1921 GTTGCTTTGTTATGGCACAGGACTGAAACGAACCCCATTTGATCCCTTACGACAAGTCTT
 739◄ hrAlaLysAsnHisCysLeuValSerValPheGlyMetGlnAspArgValValLeuArgP
1981 GGCAAGTCTAGCATTTGTAAAATTGGCTCGGCCCATTCGTGGGCTTTTGAGGTGTCCTCA
 719◄ roLeuAspLeuMetGlnLeuIleProGluAlaTrpGluHisAlaLysSerThrAspGluA
2041 GCATATCCCGGAAATCTTGCTCGCGTAATCCCGCGTAAGGTATATGTGTCGGTTTGAGCA
 699◄ laTyrGlyProPheArgAlaArgThrIleGlyArgLeuThrTyrThrAspThrGlnAlaA
2101 GCAAATGCACATACTGCTCCCTTGAAACTGGAGATAGAAATTTCTTGACTTGAGAAAGAA
 679◄ laPheAlaCysValAlaGlyLysPheSerSerIleSerIleGluGlnSerSerPheSerA
2161 GCCGTTCCGACGAATGAGCTAAAGGGGGCGGCAGTAAATACACTCCCAAAGAGCTCACAC
 659◄ laThrGlyValPheSerSerPheProAlaAlaThrPheValSerGlyPheLeuGluCysL
2221 AGCACCGCGTAACGTAAAGTATAAATTCTTTTCATCTGCTCGAAATAACTAAATATTTCT
 639◄ euValAlaTyrArgLeuThrTyrIleArgLysMetGlnGluPheTyrSerPheIleGluG
2281 TGACCGTGGACATCGCTCCCGCAAATCTCATAATTTAGATAGAATTGATCTAACGACTTA
 619◄ lnGlyHisValAspSerGlyCysIleGluTyrAsnLeuTyrPheGlnAspLeuSerLysA
2341 TCAAAAATATCGAATAAATCATCTTTGTCATTCACATCGGCATTCGGACATTCATCTTCG
 599◄ spPheIleAspPheLeuAspAspLysAspAsnValAspAlaAsnProCysGluAspGluA
2401 TTAAAACAAAATTTTTCACCATTTCCCATGTCAAAGTTCTGAGTTTCTGGCTCCGGCATT
 579◄ snPheCysPheLysGluGlyAsnGlyMetAspPheAsnGlnThrGluProGluProMetA
2461 GCTAGGGAGTACAACCTGTCATACGCCATTGTTAATTTATCTTCGGGGAGGCCCTCTGTT
 559◄ laLeuSerTyrLeuArgAspTyrAlaMetThrLeuLysAspGluProLeuGlyGluThrA
2521 CGGAGAAATTCGTAAAATTTAATCATCCCATAGTATAGCAAGGTCGACAGAAAGTGATAG
 539◄ rgLeuPheGluTyrPheLysIleMetGlyTyrTyrLeuLeuThrSerLeuPheHisTyrA
2581 GCAAATTCTACTTTGTCTTCTCCATACGTCTTGAGAAAGCTATCTTCGGATAATACATGT
 519◄ laPheGluValLysAspGluGlyTyrThrLysLeuPheSerAspGluSerLeuValHisA
2641 GCGAATTTTTCAAATGTTCCCTCAAAACCGAAGATCAATTTTTTTACCTTTTTTGTTACC
 499◄ laPheLysGluPheThrGlyGluPheGlyPheIleLeuLysLysValLysLysThrValT
2701 GTGATCTGGCTATTGAGTACGTGCGAGGCATCAGTCGTTACTAGTGTATATTCATTACTC
 479◄ hrIleGlnSerAsnLeuValHisSerAlaAspThrThrValLeuThrTyrGluAsnSerG
```

.. FIG.18 ..

2761 TCATCTCGATGGTATTCAAATCTGGGCGCGGTCACATCTAGATCCCTGCTCTGTGAATAG
459◄ luAspArgHisTyrGluPheArgProAlaThrValAspLeuAspArgSerGlnSerTyrA
2821 TTTCCAAGGCGAGAGGAATTGTTTTGCAGCCAGCGATCAATATTTAGTGTCTCTTGACCC
439◄ snGlyLeuArgSerSerAsnAsnGlnLeuTrpArgAspIleAsnLeuThrGluGlnGlyT
2881 GTCAGGGATTTATACTTTTCAAATGCCGCCATATCTACTATTGTATACATCGGCAGGAGA
419◄ hrLeuSerLysTyrLysGluPheAlaAlaMetAspValIleThrTyrMetProLeuLeuP
2941 AATACCCTATATTTTTCAGATTTCTGTGCACGAAGCTTTGCGTGCAATTTAGAAACGTAT
399◄ heValArgTyrLysGluSerLysGlnAlaArgLeuLysAlaHisLeuLysSerValTyrG
3001 TCTTTAACTTCTTCGTGGGACGAGAAAAGCCTAGTCCATCCAGGAAGCTTTGATGGATCT
379◄ luLysValGluGluHisSerSerPheLeuArgThrTrpGlyProLeuLysSerProAspL
3061 TTGATGAATGATTCTGATACAATGAACTGATCTAAGAATCTGGCATGGCGTTCTGTCAAA
359◄ ysIlePheSerGluSerValIlePheGlnAspLeuPheArgAlaHisArgGluThrLeuP
3121 GGTAACCCAAATTCAAATGCCTTTAATACTTCTCCGAAAGCAGGCTCCGAGCATCGTTTA
339◄ roLeuGlyPheGluPheAlaLysLeuValGluGlyPheAlaProGluSerCysArgLysA
3181 TTATTAATAAAGATGGCCCACTGCTTCTTGATATTCAGGACTGAAAACAGTGTAGGAGTA
319◄ snAsnIlePheIleAlaTrpGlnLysLysIleAsnLeuValSerPheLeuThrProThrC
3241 CAAATAAGATTACTTAAAATGTTTATGCTGCTGGATATAAGGTGTCGTTGATTTCTGTGC
299◄ ysIleLeuAsnSerLeuIleAsnIleSerSerSerIleLeuHisArgGlnAsnArgHisG
3301 TCGAAGCTGCTTTCCATTGCGTCTGTCTGTGTAGGGGAGCCAATGCACACGATCACTGGC
279◄ luPheSerSerGluMetAlaAspThrGlnThrProSerGlyIleCysValIleValProL
3361 TTCTTCCCGTCCTGATACATAGGCGTTTTCCACAATGCATTCATGAGCCACCACGAATAT
259◄ ysLysGlyAspGlnTyrMetProThrLysTrpLeuAlaAsnMetLeuTrpTrpSerTyrV
3421 ACTATTGCAGTCAATATATGTTTCCCTAAAACTCCAGCCTCATCAACAAGGATAATGTTG
239◄ alIleAlaThrLeuIleHisLysGlyLeuValGlyAlaGluAspValLeuIleIleAsnS
3481 CTTTTGACAAATGGAGGCATAGAGGAAATTAGGAAAGGTGCAAGGTTTACAAATTTGCGT
219◄ erLysValPheProProMetSerSerIleLeuPheProAlaLeuAsnValPheLysArgS
3541 GAAGTTTTCTGCTGGAGTGTTTGAAGGACAGACAAAGCTACCGGAGATGCCGTGTCTATG
199◄ erThrLysGlnGlnLeuThrGlnLeuValSerLeuAlaValProSerAlaThrAspIleA
3601 GCGCGTGCAGTAATGTCCTTTATCACGTCCCAATAATAATAAATGTCGGCCATTTGATGT
179◄ laArgAlaThrIleAspLysIleValAspTrpTyrTyrTyrIleAspAlaMetGlnHisG
3661 TCTGCCAACGAACGTTGTTCGTGAGGTTTTTCAAACTTGAATCGTCCTAGCACAGCCTGT
159◄ luAlaLeuSerArgGlnGluHisProLysGluPheLysPheArgGlyLeuValAlaGlnV
3721 ACGTTGTTTCCTTTGAAGCCAAAGTTTTGAAAAATAGTATGAATGGGACAAGAGGTGTAA
139◄ alAsnAsnGlyLysPheGlyPheAsnGlnPheIleThrHisIleProCysSerThrTyrS
3781 GAGGCAGATAGCTTATTGAAGATATTAAGAGCAGCTATGCGCGTTGAGCCAGTAACGATG
119◄ erAlaSerLeuLysAsnPheIleAsnLeuAlaAlaIleArgThrSerGlyThrValIleC
3841 CAATTCAATGTTTCATTAAGAGTTTGAATGCAAGTACTTTTTCCTGAGCCGGCGTTACCG
99◄ ysAsnLeuThrGluAsnLeuThrGlnIleCysThrSerLysGlySerGlyAlaAsnGlyT
3901 GTGATTAGATAAACATTAAATGGTAATTCCGCCAGAGGCAAAGTGGTCGGTTCATCTAAA
79◄ hrIleLeuTyrValAsnPheProLeuGluAlaLeuProLeuThrThrProGluAspLeuA
3961 CGTGCCACAGTCTCAAACCAAGACAGTTGCGGCTTGGAGTCTTCATGAACAGCTTGTTCT
59◄ rgAlaValThrGluPheTrpSerLeuGlnProLysSerAspGluHisValAlaGlnGluS
4021 GATAGGATTGTAATGTCCGATAAAATCGCCTGAATGCTCTGCATTGCCGAAAAATTTAAG
39◄ erLeuIleThrIleAspSerLeuIleAlaGlnIleSerGlnMetAlaSerPheAsnLeuT

UL5

4081 TAAACAGGAGTGGTGATTTCTATTTCCCGCCTGCTCTTCCCCGAAAATGGACATGCCATT
19◄ yrValProThrThrIleGluIleGluArgArgSerLysGlySerPheProCysAlaMet
4141 TTCCCAATTGCGTCAGGTACC

FIG.18

UL3

```
  1 GGTACCGAGATCCCCTCTGTGACAGAAGTTCTATATGGAGCCTCGTCTATTGACTGTGTT
  1▶ GlyThrGluIleProSerValThrGluValLeuTyrGlyAlaSerSerIleAspCysVal
 61 TCCGGATCGTACGAATGTCATGATACGCATTCTCATGTTACTCCGGACCACGCAAAAGAC
 21▶ SerGlySerTyrGluCysHisAspThrHisSerHisValThrProAspHisAlaLysAsp
121 GTAGCCGTCCAAGGGCATGTCAAAACGAATAACACCGAAGATGTAGAATCTTTGGACTCG
 41▶ ValAlaValGlnGlyHisValLysThrAsnAsnThrGluAspValGluSerLeuAspSer
181 TGTGGCTTTGACAGTGTTTTCATGATATTTTCATTCGGGGAACTCGGGAGAAGACAGCTT
 61▶ CysGlyPheAspSerValPheMetIlePheSerPheGlyGluLeuGlyArgArgGlnLeu
241 ACCGATAACATTCGAAAAGACATTTGTACTTCCCTAGACAGAGTTCCGATGGCATGTACT
 81▶ ThrAspAsnIleArgLysAspIleCysThrSerLeuAspArgValProMetAlaCysThr
301 AAGACGTCCGCATTTGCAGGTGCAAATAGACATCAGAAAAGTTTGCAGATGTTTCTCTTT
101▶ LysThrSerAlaPheAlaGlyAlaAsnArgHisGlnLysSerLeuGlnMetPheLeuPhe
361 TGCAAGAGAAGACATGCCCCGCAAATAAGGGCTCGCCTAAAAGACATTATTTCGTCAAGA
121▶ CysLysArgArgHisAlaProGlnIleArgAlaArgLeuLysAspIleIleSerSerArg
421 AAGTCAAGAAAATATTTTACGCAGTCCGAGGATGGAGAAACTCACCCCGGTGTGCCAGTT
141▶ LysSerArgLysTyrPheThrGlnSerGluAspGlyGluThrHisProGlyValProVal
481 TTCTTTCACGAGTTTGTAGCCCATGCCCCGGTATTTATTCCACGCGACAATCTTGCCCAT
161▶ PhePheHisGluPheValAlaHisAlaProValPheIleProArgAspAsnLeuAlaHis
541 GCCTGTCGCAGATTGGCCAGGCATATGACTGGAGGAATGGCGTGTTGACTTACGTGGGCG
181▶ AlaCysArgArgLeuAlaArgHisMetThrGlyGlyMetAlaCys···
601 CGCCTCTGGGTGGAACCCAGCGCTAGAACATTTATACCTGCCCCATTGCGAAAGTTACTC
```

UL3.5

```
661 AGAACGCGAATATTGCACTTCCTGGACTATGAAGTACGGTCAGGCTGCTATTGCAACTGA
                                     1▶ MetLysTyrGlyGlnAlaAlaIleAlaThrAs
721 TATGGACTTTGCCCGCATGTCTCGCCAGCCTCCACGGAAGAACTCCAGGTGCTCTTCGGC
 11▶ pMetAspPheAlaArgMetSerArgGlnProProArgLysAsnSerArgCysSerSerAl
781 ACGGACGGCTGCGTTACAGGGTAATGGATATTGCTTTCTACCGAAGTCGGAAAAGTTGCC
 31▶ aArgThrAlaAlaLeuGlnGlyAsnGlyTyrCysPheLeuProLysSerGluLysLeuPr
841 TGAGCTACCCTCTAGACATTTCGAGACCCGATTTTCCTCACTACTACCTCCAGCTGCAGC
 51▶ oGluLeuProSerArgHisPheGluThrArgPheSerSerLeuLeuProProAlaAlaAl
901 TAAGTGACAGCAACTATGAAGGTCAACTCATTTCCGCAATGCGACGCAATAATTAAATGC
 71▶ aLys···
961 TCGTATTTCATAATTTGGTGTTTATTACTTTTATTTATTCCTCTAACAGTCCGGCATGCC
                             179◀···GluGluLeuLeuGlyAlaHisAr
1021 TTGCCGCAAACTCTACAAGATCTCGAGGAACGCTTTCCTCTGGACACTCCAGCGATTCTG
 170◀ gAlaAlaPheGluValLeuAspArgProValSerGluGluProCysGluLeuSerGluPr
1081 GAGAGGATTGGGAACATGTGGGGTGGTGTGCGCGCTAGATGCTAGATCTTCCGGGGTTT
 150◀ oSerSerGlnSerCysThrProThrThrHisAlaSerSerAlaLeuAspGluProThrGl
1141 CGTATATGGTTACAGTTAAGTGAGCGACGCCCAAAAAATTCATCATGGTGATGTTGCCGC
 130◀ uTyrIleThrValThrLeuHisAlaValGlyLeuPheAsnMetMetThrIleAsnGlySe
1201 TGCTCCACCGTTCTCGCGTTCCTCCGCGCCCTAGAAACCAACATGCCGAGAACTGAAAG
 110◀ rSerTrpArgGluArgThrGlyGlyArgGlyLeuPheTrpCysAlaSerPheGlnPheAl
1261 CTAATGTTTCTCCTGAGGGTCCTCGGTGAGAACCATTGCGCTCCAAACAGTATGCGCAAA
  90◀ aLeuThrGluGlySerProGlyArgHisSerGlyAsnArgGluLeuCysTyrAlaCysPh
1321 ATTCTTCTTCACAGTCTACAGCGATCATTGTTGCGACGGGATTGTGAATTACTATTACTT
  70◀ eGluGluGluCysAspValAlaIleMetThrAlaValProAsnHisIleValIleValLy
```

FIG. 18 A

```
1381  TCCCGGGTGGTAATTGGTGGCGATACATTTTATTTCCGATGCAAATAAACCGCATTCCTC
   50◀ sGlyProProLeuGlnHisArgTyrMetLysAsnGlyIleCysIlePheArgMetGlyGl
1441  CATCGCATGAGTATACTACTTGTTCGTATTCGGTGGCCGAGCCATGCCCCAAGCCTTGGA
   30◀ yAspCysSerTyrValValGlnGluTyrGluThrAlaSerGlyHisGlyLeuGlyGlnVa
                                    UL4
1501  CTCCTACCATTACGTAGCTTATGAAAATCATGTTCTCGGGACGAGGAGGGTATGCAACAC
   10◀ lGlyValMetValTyrSerIlePheIleMet
1561  TCCAAACGACGGTGGGAAACTGATTTTAAAGCCACGCGTGTGGCTACTTTTGAGGATTAG
                                                          841◀ ...T
1621  TATACTAGTCGCGTTTCTTTGCATCTGAGCGCGCGAAGAATGTGTTGGCTTACTTGTCGA
  839◀ yrValLeuArgThrGluLysCysArgLeuAlaArgLeuIleHisGlnSerValGlnArgT
1681  GTATCTTCGTATTTCGTTCGCAGGGGGTTTAAGTTCATGCGCAAATATTCGCTACTCGTT
  819◀ hrAspGluTyrLysThrArgLeuProAsnLeuAsnMetArgLeuTyrGluSerSerThrV
1741  ACTCTAGACATTGCTACGTATGCAGTATTTAATTTCATTGTTCCGTGAGAAAAACATATT
  799◀ alArgSerMetAlaValTyrAlaThrAsnLeuLysMetThrGlyHisSerPheCysIleA
1801  GCTACCCTGTCTAAACTTAACCCTTGAGATCGTGTGATCGTCATTGCAAGGCTCGAACTT
  779◀ laValArgAspLeuSerLeuGlyGlnSerArgThrIleThrMetAlaLeuSerSerSerI
1861  ATTCCGTGGTCAATTGTTATGGCCATCCTTAATTCCTGTCCACCTATATTATCGACAAAA
  759◀ leGlyHisAspIleThrIleAlaMetArgLeuGluGlnGlyGlyIleAsnAspValPheT
1921  GTTGCTTTGTTATGGCACAGGACTGAAACGAACCCCATTTGATCCCTTACGACAAGTCTT
  739◀ hrAlaLysAsnHisCysLeuValSerValPheGlyMetGlnAspArgValValLeuArgP
1981  GGCAAGTCTAGCATTTGTAAAATTGGCTCGGCCCATTCGTGGCTTTTGAGGTGTCCTCA
  719◀ roLeuAspLeuMetGlnLeuIleProGluAlaTrpGluHisAlaLysSerThrAspGluA
2041  GCATATCCCGGAAATCTTGCTCGCGTAATCCCGCGTAAGGTATATGTGTCGGTTTGAGCA
  699◀ laTyrGlyProPheArgAlaArgThrIleGlyArgLeuThrTyrThrAspThrGlnAlaA
2101  GCAAATGCACATACTGCTCCCTTGAAACTGGAGATAGAAATTTCTTGACTTGAGAAAGAA
  679◀ laPheAlaCysValAlaGlyLysPheSerSerIleSerIleGluGlnSerSerPheSerA
2161  GCCGTTCCGACGAATGAGCTAAAGGGGGCGGCAGTAAATACACTCCCAAAGAGCTCACAC
  659◀ laThrGlyValPheSerSerPheProAlaAlaThrPheValSerGlyPheLeuGluCysL
2221  AGCACCGCGTAACGTAAAGTATAAATTCTTTTCATCTGCTCGAAATAACTAAATATTTCT
  639◀ euValAlaTyrArgLeuThrTyrIleArgLysMetGlnGluPheTyrSerPheIleGluG
2281  TGACCGTGGACATCGCTCCCGCAAATCTCATAATTTAGATAGAATTGATCTAACGACTTA
  619◀ lnGlyHisValAspSerGlyCysIleGluTyrAsnLeuTyrPheGlnAspLeuSerLysA
2341  TCAAAAATATCGAATAAATCATCTTTGTCATTCACATCGGCATTCGGACATTCATCTTCG
  599◀ spPheIleAspPheLeuAspAspLysAspAsnValAspAlaAsnProCysGluAspGluA
2401  TTAAAACAAAATTTTTCACCATTTCCCATGTCAAAGTTCTGAGTTTCTGGCTCCGGCATT
  579◀ snPheCysPheLysGluGlyAsnGlyMetAspPheAsnGlnThrGluProGluProMetA
2461  GCTAGGGAGTACAACCTGTCATACGCCATTGTTAATTTATCTTCGGGGAGGCCCTCTGTT
  559◀ laLeuSerTyrLeuArgAspTyrAlaMetThrLeuLysAspGluProLeuGlyGluThrA
2521  CGGAGAAATTCGTAAAATTTAATCATCCCATAGTATAGCAAGGTCGACAGAAAGTGATAG
  539◀ rgLeuPheGluTyrPheLysIleMetGlyTyrTyrLeuLeuThrSerLeuPheHisTyrA
2581  GCAAATTCTACTTTGTCTTCTCCATACGTCTTGAGAAAGCTATCTTCGGATAATACATGT
  519◀ laPheGluValLysAspGluGlyTyrThrLysLeuPheSerAspGluSerLeuValHisA
2641  GCGAATTTTTCAAATGTTCCCTCAAAACGAAGATCAATTTTTTTACCTTTTTTGTTACC
  499◀ laPheLysGluPheThrGlyGluPheGlyPheIleLeuLysLysValLysLysThrValT
2701  GTGATCTGGCTATTGAGTACGTGCGAGGCATCAGTCGTTACTAGTGTATATTCATTACTC
  479◀ hrIleGlnSerAsnLeuValHisSerAlaAspThrThrValLeuThrTyrGluAsnSerG
```

FIG. 18 B

```
2761 TCATCTCGATGGTATTCAAATCTGGGCGCGGTCACATCTAGATCCCTGCTCTGTGAATAG
 459◀ luAspArgHisTyrGluPheArgProAlaThrValAspLeuAspArgSerGlnSerTyrA
2821 TTTCCAAGGCGAGAGGAATTGTTTTGCAGCCAGCGATCAATATTTAGTGTCTCTTGACCC
 439◀ snGlyLeuArgSerSerAsnAsnGlnLeuTrpArgAspIleAsnLeuThrGluGlnGlyT
2881 GTCAGGGATTTATACTTTTCAAATGCCGCCATATCTACTATTGTATACATCGGCAGGAGA
 419◀ hrLeuSerLysTyrLysGluPheAlaAlaMetAspValIleThrTyrMetProLeuLeuP
2941 AATACCCTATATTTTTCAGATTTCTGTGCACGAAGCTTTGCGTGCAATTTAGAAACGTAT
 399◀ heValArgTyrLysGluSerLysGlnAlaArgLeuLysAlaHisLeuLysSerValTyrG
3001 TCTTTAACTTCTTCGTGGGACGAGAAAAGCCTAGTCCATCCAGGAAGCTTTGATGGATCT
 379◀ luLysValGluGluHisSerSerPheLeuArgThrTrpGlyProLeuLysSerProAspL
3061 TTGATGAATGATTCTGATACAATGAACTGATCTAAGAATCTGGCATGGCGTTCTGTCAAA
 359◀ ysIlePheSerGluSerValIlePheGlnAspLeuPheArgAlaHisArgGluThrLeuP
3121 GGTAACCCAAATTCAAATGCCTTTAATACTTCTCCGAAAGCAGGCTCCGAGCATCGTTTA
 339◀ roLeuGlyPheGluPheAlaLysLeuValGluGlyPheAlaProGluSerCysArgLysA
3181 TTATTAATAAAGATGGCCCACTGCTTCTTGATATTCAGGACTGAAAACAGTGTAGGAGTA
 319◀ snAsnIlePheIleAlaTrpGlnLysLysIleAsnLeuValSerPheLeuThrProThrC
3241 CAAATAAGATTACTTAAAATGTTTATGCTGCTGGATATAAGGTGTCGTTGATTTCTGTGC
 299◀ ysIleLeuAsnSerLeuIleAsnIleSerSerIleLeuHisArgGlnAsnArgHisG
3301 TCGAAGCTGCTTTCCATTGCGTCTGTCTGTGTAGGGGAGCCAATGCACACGATCACTGGC
 279◀ luPheSerSerGluMetAlaAspThrGlnThrProSerGlyIleCysValIleValProL
3361 TTCTTCCCGTCCTGATACATAGGCGTTTTCCACAATGCATTCATGAGCCACCACGAATAT
 259◀ ysLysGlyAspGlnTyrMetProThrLysTrpLeuAlaAsnMetLeuTrpTrpSerTyrV
3421 ACTATTGCAGTCAATATATGTTTCCCTAAAACTCCAGCCTCATCAACAAGGATAATGTTG
 239◀ alIleAlaThrLeuIleHisLysGlyLeuValGlyAlaGluAspValLeuIleIleAsnS
3481 CTTTTGACAAATGGAGGCATAGAGGAAATTAGGAAAGGTGCAAGGTTTACAAATTTGCGT
 219◀ erLysValPheProProMetSerSerIleLeuPheProAlaLeuAsnValPheLysArgS
3541 GAAGTTTTCTGCTGGAGTGTTTGAAGGACAGACAAAGCTACCGGAGATGCCGTGTCTATG
 199◀ erThrLysGlnGlnLeuThrGlnLeuValSerLeuAlaValProSerAlaThrAspIleA
3601 GCGCGTGCAGTAATGTCCTTTATCACGTCCCAATAATAATAAATGTCGGCCATTTGATGT
 179◀ laArgAlaThrIleAspLysIleValAspTrpTyrTyrTyrIleAspAlaMetGlnHisG
3661 TCTGCCAACGAACGTTGTTCGTGAGGTTTTTCAAACTTGAATCGTCCTAGCACAGCCTGT
 159◀ luAlaLeuSerArgGlnGluHisProLysGluPheLysPheArgGlyLeuValAlaGlnV
3721 ACGTTGTTTCCTTTGAAGCCAAAGTTTTGAAAAATAGTATGAATGGGACAAGAGGTGTAA
 139◀ alAsnAsnGlyLysPheGlyPheAsnGlnPheIleThrHisIleProCysSerThrTyrS
3781 GAGGCAGATAGCTTATTGAAGATATTAAGAGCAGCTATGCGCGTTGAGCCAGTAACGATG
 119◀ erAlaSerLeuLysAsnPheIleAsnLeuAlaAlaIleArgThrSerGlyThrValIleC
3841 CAATTCAATGTTTCATTAAGAGTTTGAATGCAAGTACTTTTTCCTGAGCCGGCGTTACCG
  99◀ ysAsnLeuThrGluAsnLeuThrGlnIleCysThrSerLysGlySerGlyAlaAsnGlyT
3901 GTGATTAGATAAACATTAAATGGTAATTCCGCCAGAGGCAAAGTGGTCGGTTCATCTAAA
  79◀ hrIleLeuTyrValAsnPheProLeuGluAlaLeuProLeuThrThrProGluAspLeuA
3961 CGTGCCACAGTCTCAAACCAAGACAGTTGCGGCTTGGAGTCTTCATGAACAGCTTGTTCT
  59◀ rgAlaValThrGluPheTrpSerLeuGlnProLysSerAspGluHisValAlaGlnGluS
4021 GATAGGATTGTAATGTCCGATAAAATCGCCTGAATGCTCTGCATTGCCGAAAAATTTAAG
  39◀ erLeuIleThrIleAspSerLeuIleAlaGlnIleSerGlnMetAlaSerPheAsnLeuT
                                                              UL5
4081 TAAACAGGAGTGGTGATTTCTATTTCCCGCCTGCTCTTCCCCGAAAATGGACATGCCATT
  19◀ yrValProThrThrIleGluIleGluArgArgSerLysGlySerPheProCysAlaMet
4141 TTCCCAATTGCGTCAGGTACC
```

FIG. 18 C

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 4161 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Infectious Laryngotracheitis Virus
      (B) STRAIN: T20 Select Laboratories (ix) FEATURE:
      (A) NAME/KEY: CDS
      (B) LOCATION:1..585
      (D) OTHER INFORMATION:/partial
         /product= "ORFA"
         /gene= "ORFA"

(ix) FEATURE:
      (A) NAME/KEY: CDS
      (B) LOCATION:689..904
      (D) OTHER INFORMATION:/product= "ORFB"
         /gene= "ORFB"

(ix) FEATURE:
      (A) NAME/KEY: CDS
      (B) LOCATION:complement (998..1531)
      (D) OTHER INFORMATION:/product= "ORFC"
         /gene= "ORFC"

(ix) FEATURE:
      (A) NAME/KEY: CDS
      (B) LOCATION:complement (1620..4160)
      (D) OTHER INFORMATION:/partial
         /product= "ORFD"
         /gene= "ORFD"

(xi) SEQUENCE DESCRIPTION: SEQ ID NO: 1:

```
GGTACCGAGA TCCCCTCTGT GACAGAAGTT CTATATGGAG CCTCGTCTAT TGACTGTGTT        60

TCCGGATCGT ACGAATGTCA TGATACGCAT TCTCATGTTA CTCCGGACCA CGCAAAAGAC       120

GTAGCCGTCC AAGGGCATGT CAAAACGAAT AACACCGAAG ATGTAGAATC TTTGGACTCG       180

TGTGGCTTTG ACAGTGTTTT CATGATATTT TCATTCGGGG AACTCGGGAG AAGACAGCTT       240

ACCGATAACA TTCGAAAAGA CATTTGTACT TCCCTAGACA GAGTTCCGAT GGCATGTACT       300
```

-continued

```
AAGACGTCCG CATTTGCAGG TGCAAATAGA CATCAGAAAA GTTTGCAGAT GTTTCTCTTT    360

TGCAAGAGAA GACATGCCCC GCAAATAAGG GCTCGCCTAA AAGACATTAT TTCGTCAAGA    420

AAGTCAAGAA AATATTTTAC GCAGTCCGAG GATGGAGAAA CTCACCCCGG TGTGCCAGTT    480

TTCTTTCACG AGTTTGTAGC CCATGCCCCG GTATTTATTC CACGCGACAA TCTTGCCCAT    540

GCCTGTCGCA GATTGGCCAG GCATATGACT GGAGGAATGG CGTGTTGACT TACGTGGGCG    600

CGCCTCTGGG TGGAACCCAG CGCTAGAACA TTTATACCTG CCCCATTGCG AAAGTTACTC    660

AGAACGCGAA TATTGCACTT CCTGGACTAT GAAGTACGGT CAGGCTGCTA TTGCAACTGA    720

TATGGACTTT GCCCGCATGT CTCGCCAGCC TCCACGGAAG AACTCCAGGT GCTCTTCGGC    780

ACGGACGGCT GCGTTACAGG GTAATGGATA TTGCTTTCTA CCGAAGTCGG AAAAGTTGCC    840

TGAGCTACCC TCTAGACATT TCGAGACCCG ATTTTCCTCA CTACTACCTC CAGCTGCAGC    900

TAAGTGACAG CAACTATGAA GGTCAACTCA TTTCCGCAAT GCGACGCAAT AATTAAATGC    960

TCGTATTTCA TAATTTGGTG TTTATTACTT TTATTTATTC CTCTAACAGT CCGGCATGCC   1020

TTGCCGCAAA CTCTACAAGA TCTCGAGGAA CGCTTTCCTC TGGACACTCC AGCGATTCTG   1080

GAGAGGATTG GGAACATGTG GGGGTGGTGT GCGCGCTAGA TGCTAGATCT TCCGGGGTTT   1140

CGTATATGGT TACAGTTAAG TGAGCGACGC CCAAAAAATT CATCATGGTG ATGTTGCCGC   1200

TGCTCCACCG TTCTCGCGTT CCTCCGCGCC CTAGAAACCA ACATGCCGAG AACTGAAAAG   1260

CTAATGTTTC TCCTGAGGGT CCTCGGTGAG AACCATTGCG CTCCAAACAG TATGCGCAAA   1320

ATTCTTCTTC ACAGTCTACA GCGATCATTG TTGCGACGGG ATTGTGAATT ACTATTACTT   1380

TCCCGGGTGG TAATTGGTGG CGATACATTT TATTTCCGAT GCAAATAAAC CGCATTCCTC   1440

CATCGCATGA GTATACTACT TGTTCGTATT CGGTGGCCGA GCCATGCCCC AAGCCTTGGA   1500

CTCCTACCAT TACGTAGCTT ATGAAAATCA TGTTCTCGGG ACGAGGAGGG TATGCAACAC   1560

TCCAAACGAC GGTGGGAAAC TGATTTTAAA GCCACGCGTG TGGCTACTTT TGAGGATTAG   1620

TATACTAGTC GCGTTTCTTT GCATCTGAGC GCGCGAAGAA TGTGTTGGCT TACTTGTCGA   1680

GTATCTTCGT ATTTCGTTCG CAGGGGGTTT AAGTTCATGC GCAAATATTC GCTACTCGTT   1740

ACTCTAGACA TTGCTACGTA TGCAGTATTT AATTTCATTG TTCCGTGAGA AAAACATATT   1800

GCTACCCTGT CTAAACTTAA CCCTTGAGAT CGTGTGATCG TCATTGCAAG GCTCGAACTT   1860

ATTCCGTGGT CAATTGTTAT GGCCATCCTT AATTCCTGTC CACCTATATT ATCGACAAAA   1920

GTTGCTTTGT TATGGCACAG GACTGAAACG AACCCCATTT GATCCCTTAC GACAAGTCTT   1980

GGCAAGTCTA GCATTTGTAA AATTGGCTCG GCCCATTCGT GGGCTTTTGA GGTGTCCTCA   2040

GCATATCCCG GAAATCTTGC TCGCGTAATC CCGCGTAAGG TATATGTGTC GGTTTGAGCA   2100

GCAAATGCAC ATACTGCTCC CTTGAAACTG GAGATAGAAA TTTCTTGACT TGAGAAAGAA   2160

GCCGTTCCGA CGAATGAGCT AAAGGGGGCG GCAGTAAATA CACTCCCAAA GAGCTCACAC   2220

AGCACCGCGT AACGTAAAGT ATAAATTCTT TTCATCTGCT CGAAATAACT AAATATTTCT   2280

TGACCGTGGA CATCGCTCCC GCAAATCTCA TAATTTAGAT AGAATTGATC TAACGACTTA   2340

TCAAAAATAT CGAATAAATC ATCTTTGTCA TTCACATCGG CATTCGGACA TTCATCTTCG   2400

TTAAAACAAA ATTTTTCACC ATTTCCCATG TCAAAGTTCT GAGTTTCTGG CTCCGGCATT   2460

GCTAGGGAGT ACAACCTGTC ATACGCCATT GTTAATTTAT CTTCGGGGAG GCCCTCTGTT   2520

CGGAGAAATT CGTAAAATTT AATCATCCCA TAGTATAGCA AGGTCGACAG AAAGTGATAG   2580

GCAAATTCTA CTTTGTCTTC TCCATACGTC TTGAGAAAGC TATCTTCGGA TAATACATGT   2640
```

-continued

```
GCGAATTTTT CAAATGTTCC CTCAAAACCG AAGATCAATT TTTTTACCTT TTTTGTTACC      2700

GTGATCTGGC TATTGAGTAC GTGCGAGGCA TCAGTCGTTA CTAGTGTATA TTCATTACTC      2760

TCATCTCGAT GGTATTCAAA TCTGGGCGCG GTCACATCTA GATCCCTGCT CTGTGAATAG      2820

TTTCCAAGGC GAGAGGAATT GTTTTGCAGC CAGCGATCAA TATTTAGTGT CTCTTGACCC      2880

GTCAGGGATT TATACTTTTC AAATGCCGCC ATATCTACTA TTGTATACAT CGGCAGGAGA      2940

AATACCCTAT ATTTTTCAGA TTTCTGTGCA CGAAGCTTTG CGTGCAATTT AGAAACGTAT      3000

TCTTTAACTT CTTCGTGGGA CGAGAAAAGC CTAGTCCATC CAGGAAGCTT TGATGGATCT      3060

TTGATGAATG ATTCTGATAC AATGAACTGA TCTAAGAATC TGGCATGGCG TTTTGTCAAA      3120

GGTAACCCAA ATTCAAATGC CTTTAATACT CTCCGAAAG CAGGCTCCGA GCATCGTTTA       3180

TTATTAATAA AGATGGCCCA CTGCTTCTTG ATATTCAGGA CTGAAAACAG TGTAGGAGTA      3240

CAAATAAGAT TACTTAAAAT GTTTATGCTG CTGGATATAA GGTGTCGTTG ATTTCTGTGC      3300

TCGAAGCTGC TTTCCATTGC GTCTGTCTGT GTAGGGGAGC CAATGCACAC GATCACTGGC      3360

TTCTTCCCGT CCTGATACAT AGGCGTTTTC CACAATGCAT TCATGAGCCA CCACGAATAT      3420

ACTATTGCAG TCAATATATG TTTCCCTAAA ACTCCAGCCT CATCAACAAG GATAATGTTG      3480

CTTTTGACAA ATGGAGGCAT AGAGGAAATT AGGAAAGGTG CAAGGTTTAC AAATTTGCGT      3540

GAAGTTTTCT GCTGGAGTGT TTGAAGGACA GACAAAGCTA CCGGAGATGC CGTGTCTATG      3600

GCGCGTGCAG TAATGTCCTT TATCACGTCC CAATAATAAT AAATGTCGGC CATTTGATGT      3660

TCTGCCAACG AACGTTGTTC GTGAGGTTTT TCAAACTTGA ATCGTCCTAG CACAGCCTGT      3720

ACGTTGTTTC CTTTGAAGCC AAAGTTTTGA AAAATAGTAT GAATGGGACA AGAGGTGTAA      3780

GAGGCAGATA GCTTATTGAA GATATTAAGA GCAGCTATGC GCGTTGAGCC AGTAACGATG      3840

CAATTCAATG TTTCATTAAG AGTTTGAATG CAAGTACTTT TTCCTGAGCC GGCGTTACCG      3900

GTGATTAGAT AAACATTAAA TGGTAATTCC GCCAGAGGCA AAGTGGTCGG TTCATCTAAA      3960

CGTGCCACAG TCTCAAACCA AGACAGTTGC GGCTTGGAGT CTTCATGAAC AGCTTGTTCT      4020

GATAGGATTG TAATGTCCGA TAAAATCGCC TGAATGCTCT GCATTGCCGA AAAATTTAAG      4080

TAAACAGGAG TGGTGATTTC TATTTCCCGC CTGCTCTTCC CCGAAAATGG ACATGCCATT      4140

TTCCCAATTG CGTCAGGTAC C                                                4161
```

(2) INFORMATION FOR SEQ ID NO: 2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Infectious laryngotracheitis virus (xi) SEQUENCE DESCRIPTION: SEQ ID NO: 2:

```
TATTGCTTTC TACCGAAGTC GG                                                 22
```

(2) INFORMATION FOR SEQ ID NO: 3:

(i) SEQUENCE CHARACTERISTICS:
        (A) LENGTH: 34 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (vi) ORIGINAL SOURCE:
        (A) ORGANISM: Infectious laryngotracheitis virus (xi) SEQUENCE DESCRIPTION: SEQ ID NO: 3:

ACGCGAATTC AAATACGAGC ATTTAATTAT TGCG                                34

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Infectious laryngotracheitis virus (xi) SEQUENCE DESCRIPTION: SEQ ID NO: 4:

TCTCCAGAAT CGCTGGAGTG TCC                                           23

(2) INFORMATION FOR SEQ ID NO: 5:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (vi) ORIGINAL SOURCE:
        (A) ORGANISM: Infectious laryngotracheitis virus (xi) SEQUENCE DESCRIPTION: SEQ ID NO: 5:

TGCGCGAATT CGTAAGCTTT GATATCCAGT CGACATAATT TGGTGTTTAT TACTTTTA     58

(2) INFORMATION FOR SEQ ID NO: 6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO: 6:

CGAATTCACT AGTGTGTGTC TGCAGGCGGC CGCGTGTGTG TCGACGGTAC              50

(2) INFORMATION FOR SEQ ID NO: 7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (xi) SEQUENCE DESCRIPTION: SEQ ID NO: 7:

```
CGTCGACACA CACGCGGCCG CCTGCAGACA CACACTAGTG AATTCGAGCT          50
```

(2) INFORMATION FOR SEQ ID NO: 8:

(i) SEQUENCE CHARACTERISTICS:
        (A) LENGTH: 2521 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Newcastle disease virus
        (B) STRAIN: Texas GB (ix) FEATURE:
        (A) NAME/KEY: CDS
        (B) LOCATION:303..2006
        (D) OTHER INFORMATION:/function= "Hemagglutinin
            Neuraminidase"
            /product= "HN"
            /gene= "HN"
            /standard_name= "HN"

(xi) SEQUENCE DESCRIPTION: SEQ ID NO: 8:

```
TGCTACCTGA TGTACAAGCA AAAGGCACAA CAAAAGACCT TGTTATGGCT TGGGAATAAT     60

ACCCTTGATC AGATGAGAGC CACTACAAAA ATATGAATAC AAACGAGAGG CGGAGGTATC    120

CCCAATAGCA ATTTGCGTGT AAATTCTGGC AACCTGTTAA TTAGAAGAAT TAAGAAAAAA    180

CCACTGGATG TAAGTGACAA CAAGCAATA CACGGGTAGA ACGGTCGGAG AAGCCACCCC     240

TCAATCGGGA ATCAGGCCTC ACAACGTCCT TTCTACCGCA TCATCAATAG CAGACTTCGG    300

TCATGGACCG TGCAGTTAGC AGAGTTGCGC TAGAGAATGA AGAAAGAGAA GCAAAGAATA    360

CATGGCGCTT TGTATTCCGG ATTGCAATCT TACTTTTAAT AGTAACAACC TTAGCCATCT    420

CTGCAACCGC CCTGGTATAT AGCATGGAGG CTAGCACGCC TGGCGACCTT GTTGGCATAC    480

CGACTATGAT CTCTAAGGCA GAAGAAAAGA TTACATCTGC ACTCAGTTCT AATCAAGATG    540

TAGTAGATAG GATATATAAG CAGGTGGCCC TTGAGTCTCC ATTGGCGTTG CTAAACACTG    600

AATCTGTAAT TATGAATGCA ATAACGTCTC TCTCTTATCA AATCAATGGA GCTGCAAATA    660

ATAGCGGGTG TGGGGCACCT GTTCATGACC CAGATTATAT CGGGGGGATA GGCAAAGAAC    720

TTATTGTGGA TGACGCTAGT GATGTCACAT CATTCTATCC CTCTGCGTTC CAAGAACACC    780

TGAACTTTAT CCCGGCACCT ACTACAGGAT CAGGTTGCAC TCGGATACCC TCATTCGACA    840

TAAGCGCTAC CCACTACTGT TACACTCACA ATGTGATATT ATCTGGTTGC AGAGATCACT    900
```

-continued

```
CACACTCATA TCAGTACTTA GCACTTGGCG TGCTTCGGAC ATCTGCAACA GGGAGGGTAT    960

TCTTTTCTAC TCTGCGTTCC ATCAATTTGG ATGACAGCCA AAATCGGAAG TCTTGCAGTG   1020

TGAGTGCAAC TCCCTTAGGT TGTGATATGC TGTGCTCTAA AATCACAGAG ACTGAGGAAG   1080

AGGATTATAG TTCAATTACG CCTACATCGA TGGTGCACGG AAGGTTAGGG TTTGACGGTC   1140

AATACCATGA GAAGGACTTA GACGTCATAA CTTTATTTAA GGATTGGGTG GCAAATTACC   1200

CAGGAGTGGG GGGTGGGTCT TTTATTAACA ACCGCGTATG GTTCCCAGTC TACGGAGGGC   1260

TAAAACCCAA TTCGCCTAGT GACACCGCAC AAGAAGGGAG ATATGTAATA TACAAGCGCT   1320

ACAATGACAC ATGCCCAGAT GAACAAGATT ACCAGATTCG GATGGCTAAG TCTTCATATA   1380

AGCCTGGGCG GTTTGGTGGA AAACGCGTAC AGCAGGCCAT CTTATCTATC AAGGTGTCAA   1440

CATCTTTGGG CGAGGACCCG GTGCTGACTG TACCGCCTAA TACAATCACA CTCATGGGGG   1500

CCGAAGGCAG AGTTCTCACA GTAGGGACAT CTCATTTCTT GTACCAGCGA GGGTCTTCAT   1560

ACTTCTCTCC TGCTTTATTA TACCCTATGA CAGTCAACAA CAAAACGGCT ACTCTTCATA   1620

GTCCTTACAC ATTCAATGCT TTCACTAGGC CAGGTAGTGT CCCTTGTCAG GCATCAGCAA   1680

GATGCCCCAA CTCATGTGTC ACTGGAGTTT ATACTGATCC GTATCCCTTA GTCTTCCATA   1740

GGAACCATAC CTTGCGGGGG GTATTCGGGA CAATGCTTGA TGATGAACAA GCAAGACTTA   1800

ACCCTGTATC TGCAGTATTT GATAACATAT CCCGCAGTCG CATAACCCGG GTAAGTTCAA   1860

GCCGTACTAA GGCAGCATAC ACGACATCGA CATGTTTTAA AGTTGTCAAG ACCAATAAAA   1920

CATATTGCCT CAGCATTGCA GAAATATCCA ATACCCTCTT CGGGGAATTC AGGATCGTTC   1980

CTTTACTAGT TGAGATTCTC AAGGATGATG GGATTTAAGA AGCTTGGTCT GGCCAGTTGA   2040

GTCAACTGCG AGAGGGTCGG AAAGATGACA TTGTGTCACC TTTTTTTTGT AATGCCAAGG   2100

ATCAAACTGG ATACCGGCGC GAGCCCGAAT CCTATGCTGC CAGTCAGCCA TAATCAGATA   2160

GTACTAATAT GATTAGTCTT AATCTTGTCG ATAGTAACTT GGTTAAGAAA AAATATGAGT   2220

GGTAGTGAGA TACACAGCTA AACAACTCAC GAGAGATAGC ACGGGTAGGA CATGGCGAGC   2280

TCCGGTCCCG AAAGGGCAGA GCATCAGATT ATCCTACCAG AGTCACATCT GTCCTCACCA   2340

TTGGTCAAGC ACAAACTGCT CTATTACTGG AAATTAACTG GCGTACCGCT TCCTGACGAA   2400

TGTGACTTCG ACCACCTCAT TATCAGCCGA CAATGGAAGA AAATACTTGA ATCGGCCACT   2460

CCTGACACTG AGAGGATGAT AAAGCTCGGG CGGGCAGTAC ACCAGACTCT CGACCACCGC   2520

C                                                                  2521
```

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Newcastle Disease Virus
        (B) STRAIN: Texas GB (xi) SEQUENCE DESCRIPTION: SEQ ID NO: 9:

```
CAGACCAAGC TTCTTAAATC CC                                             22
```

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (vi) ORIGINAL SOURCE:
        (A) ORGANISM: Newcastle Disease Virus
        (B) STRAIN: Texas GB (xi) SEQUENCE DESCRIPTION: SEQ ID NO: 10:

GTATTCGGGA CAATGC                                      16

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (vi) ORIGINAL SOURCE:
        (A) ORGANISM: Newcastle Disease Virus
        (B) STRAIN: Texas GB (xi) SEQUENCE DESCRIPTION: SEQ ID NO: 11:

GTGACATCAC TAGCGTCATC C                              21

(2) INFORMATION FOR SEQ ID NO: 12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: YES (vi) ORIGINAL SOURCE:
        (A) ORGANISM: Newcastle Disease Virus
        (B) STRAIN: Texas GB (xi) SEQUENCE DESCRIPTION: SEQ ID NO: 12:

CCGCATCATC AGCGGCCGCG ATCGGTCATG GACAGT                36

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear

```
    (ii) MOLECULE TYPE: DNA (genomic)

(iii) HYPOTHETICAL: YES (iv) ANTI-SENSE: NO (vi) ORIGINAL SOURCE:
         (A) ORGANISM: Newcastle Disease Virus
         (B) STRAIN: Texas GB (xi) SEQUENCE DESCRIPTION: SEQ ID NO: 13:

TGACCCTGTC TGGGATGA                                                    18

-continued (xi) SEQUENCE DESCRIPTION: SEQ ID NO: 16:

TTCGGGACAT TTTCGCGG 18

(2) INFORMATION FOR SEQ ID NO: 17:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (vi) ORIGINAL SOURCE:
(A) ORGANISM: Marek's Disease Virus
(B) STRAIN: RB1B (xi) SEQUENCE DESCRIPTION: SEQ ID NO: 17:

TATATGGCGT TAGTCTCC 18

(2) INFORMATION FOR SEQ ID NO: 18:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: YES (vi) ORIGINAL SOURCE:
(A) ORGANISM: Marek's Disease Virus
(B) STRAIN: RB1B (xi) SEQUENCE DESCRIPTION: SEQ ID NO: 18:

TTGCGAGCTC GCGGCCGCTT ATTACACAGC ATCATCTTCT G 41

(2) INFORMATION FOR SEQ ID NO: 19:

(i) SEQUENCE CHARACTERISTICS:
(A) LENGTH: 4161 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Infectious Laryngotracheitis Virus
(B) STRAIN: Lutticken (xi) SEQUENCE DESCRIPTION: SEQ ID NO: 19:

GGTACCTGAC GCAATTGGGA AAATGGCATG TCCATTTTCG GGGAAGAGCA GGCGGGAAAT 60

AGAAATCACC ACTCCTGTTT ACTTAAATTT TTCGGCAATG CAGAGCATTC AGGCGATTTT 120

ATCGGACATT ACAATCCTAT CAGAACAAGC TGTTCATGAA GACTCCAAGC CGCAACTGTC 180

TTGGTTTGAG ACTGTGGCAC GTTTAGATGA ACCGACCACT TTGCCTCTGG CGGAATTACC 240

```
ATTTAATGTT TATCTAATCA CCGGTAACGC CGGCTCAGGA AAAAGTACTT GCATTCAAAC    300

TCTTAATGAA ACATTGAATT GCATCGTTAC TGGCTCAACG CGCATAGCTG CTCTTAATAT    360

CTTCAATAAG CTATCTGCCT CTTACACCTC TTGTCCCATT CATACTATTT TTCAAAACTT    420

TGGCTTCAAA GGAAACAACG TACAGGCTGT GCTAGGACGA TTCAAGTTTG AAAAACCTCA    480

CGAACAACGT TCGTTGGCAG AACATCAAAT GGCCGACATT TATTATTATT GGGACGTGAT    540

AAAGGACATT ACTGCACGCG CCATAGACAC GGCATCTCCG GTAGCTTTGT CTGTCCTTCA    600

AACACTCCAG CAGAAAACTT CACGCAAATT TGTAAACCTT GCACCTTTCC TAATTTCCTC    660

TATGCCTCCA TTTGTCAAAA GCAACATTAT CCTTGTTGAT GAGGCTGGAG TTTTAGGGAA    720

ACATATATTG ACTGCAATAG TATATTCGTG GTGGCTCATG AATGCATTGT GGAAAACGCC    780

TATGTATCAG GACGGGAAGA AGCCAGTGAT CGTGTGCATT GGCTCCCCTA CACAGACAGA    840

CGCAATGGAA AGCAGCTTCG AGCACAGAAA TCAACGACAC CTTATATCCA GCAGCATAAA    900

CATTTTAAGT AATCTTATTT GTACTCCTAC ACTGTTTTCA GTCCTGAATA TCAAGAAGCA    960

GTGGGCCATC TTTATTAATA ATAAACGATG CTCGGAGCCT GCTTTCGGAG AAGTATTAAA   1020

GGCATTTGAA TTTGGGTTAC CTTTGACAGA ACGCCATGCC AGATTCTTAG ATCAGTTCAT   1080

TGTATCAGAA TCATTCATCA AAGATCCATC AAAGCTTCCT GGATGGACTA GGCTTTTCTC   1140

GTCCCACGAA GAAGTTAAAG AATACGTTTC TAAATTGCAC GCAAAGCTTC GTGCACAGAA   1200

ATCTGAAAAA TATAGGGTAT TTCTCCTGCC GATGTATACA ATAGTAGATA TGGCGGCATT   1260

TGAAAAGTAT AAATCCCTGA CGGGTCAAGA GACACTAAAT ATTGATCGCT GGCTGCAAAA   1320

CAATTCCTCT CGCCTTGGAA ACTATTCACA GAGCAGGGAT CTAGATGTGA CCGCGCCCAG   1380

ATTTGAATAC CATCGAGATG AGAGTAATGA ATATACACTA GTAACGACTG ATGCCTCGCA   1440

CGTACTCAAT AGCCAGATCA CGGTAACAAA AAAGGTAAAA AAATTGATCT TCGGTTTTGA   1500

GGGAACATTT GAAAAATTCG CACATGTATT ATCCGAAGAT AGCTTTCTCA AGACGTATGG   1560

AGAAGACAAA GTAGAATTTG CCTATCACTT TCTGTCGACC TTGCTATACT ATGGGATGAT   1620

TAAATTTTAC GAATTTCTCC GAACAGAGGG CCTCCCCGAA GATAAATTAA CAATGGCGTA   1680

TGACAGGTTG TACTCCCTAG CAATGCCGGA GCCAGAAACT CAGAACTTTG ACATGGGAAA   1740

TGGTGAAAAA TTTTGTTTTA ACGAAGATGA ATGTCCGAAT GCCGATGTGA ATGACAAAGA   1800

TGATTTATTC GATATTTTTG ATAAGTCGTT AGATCAATTC TATCTAAATT ATGAGATTTG   1860

CGGGAGCGAT GTCCACGGTC AAGAAATATT TAGTTATTTC GAGCAGATGA AAAGAATTTA   1920

TACTTTACGT TACGCGGTGC TGTGTGAGCT CTTTGGGAGT GTATTTACTG CCGCCCCCTT   1980

TAGCTCATTG GTCGGAACGG CTTCTTTCTC AAGTCAAGAA ATTTCTATCT CCAGTTTCAA   2040

GGGAGCAGTA TGTGCATTTG CTGCTCAAAC CGACACATAT ACCTTACGCG GGATTACGCG   2100

AGCAAGATTT CCGGGATATG CTGAGGACAC CTCAAAAGCC CACGAATGGG CCGAGCCAAT   2160

TTTACAAATG CTAGACTTGC CAAGACTTGT CGTAAGGGAT CAAATGGGGT TCGTTTCAGT   2220

CCTGTGCCAT AACAAAGCAA CTTTTGTCGA TAATATAGGT GGACAGGAAT TAAGGATGGC   2280

CATAACAATT GACCACGGAA TAAGTTCGAG CCTTGCAATG ACGATCACAC GATCTCAAGG   2340

GTTAAGTTTA GACAGGGTAG CAATATGTTT TTCTCACGGA ACAATGAAAT TAAATACTGC   2400

ATACGTAGCA ATGTCTAGAG TAACGAGTAG CGAATATTTG CGCATGAACT TAAACCCCCT   2460

GCGAACGAAA TACGAAGATA CTCGACAAGT AAGCCAACAC ATTCTTCGCG CGCTCAGATG   2520

CAAAGAAACG CGACTAGTAT ACTAATCCTC AAAAGTAGCC ACACGCGTGG CTTTAAAATC   2580

AGTTTCCCAC CGTCGTTTGG AGTGTTGCAT ACCCTCCTCG TCCCGAGAAC ATGATTTTCA   2640
```

-continued

```
TAAGCTACGT AATGGTAGGA GTCCAAGGCT TGGGGCATGG CTCGGCCACC GAATACGAAC    2700

AAGTAGTATA CTCATGCGAT GGAGGAATGC GGTTTATTTG CATCGGAAAT AAAATGTATC    2760

GCCACCAATT ACCACCCGGG AAAGTAATAG TAATTCACAA TCCCGTCGCA ACAATGATCG    2820

CTGTAGACTG TGAAGAAGAA TTTTGCGCAT ACTGTTTGGA GCGCAATGGT TCTCACCGAG    2880

GACCCTCAGG AGAAACATTA GCTTTTCAGT TCTCGGCATG TTGGTTTCTA GGGCGCGGAG    2940

GAACGCGAGA ACGGTGGAGC AGCGGCAACA TCACCATGAT GAATTTTTTG GGCGTCGCTC    3000

ACTTAACTGT AACCATATAC GAAACCCCGG AAGATCTAGC ATCTAGCGCG CACACCACCC    3060

CCACATGTTC CCAATCCTCT CCAGAATCGC TGGAGTGTCC AGAGGAAAGC GTTCCTCGAG    3120

ATCTTGTAGA GTTTGCGGCA AGGCATGCCG GACTGTTAGA GGAATAAATA AAAGTAATAA    3180

ACACCAAATT ATGAAATACG AGCATTTAAT TATTGCGTCG CATTGCGGAA ATGAGTTGAC    3240

CTTCATAGTT GCTGTCACTT AGCTGCAGCT GGAGGTAGTA GTGAGGAAAA TCGGGTCTCG    3300

AAATGTCTAG AGGGTAGCTC AGGCAACTTT TCCGACTTCG GTAGAAAGCA ATATCCATTA    3360

CCCTGTAACG CAGCCGTCCG TGCCGAAGAG CACCTGGAGT TCTTCCGTGG AGGCTGGCGA    3420

GACATGCGGG CAAAGTCCAT ATCAGTTGCA ATAGCAGCCT GACCGTACTT CATAGTCCAG    3480

GAAGTGCAAT ATTCGCGTTC TGAGTAACTT TCGCAATGGG GCAGGTATAA ATGTTCTAGC    3540

GCTGGGTTCC ACCCAGAGGC GCGCCCACGT AAGTCAACAC GCCATTCCTC CAGTCATATG    3600

CCTGGCCAAT CTGCGACAGG CATGGGCAAG ATTGTCGCGT GGAATAAATA CCGGGGCATG    3660

GGCTACAAAC TCGTGAAAGA AAACTGGCAC ACCGGGGTGA GTTTCTCCAT CCTCGGACTG    3720

CGTAAAATAT TTTCTTGACT TTCTTGACGA AATAATGTCT TTTAGGCGAG CCCTTATTTG    3780

CGGGGCATGT CTTCTCTTGC AAAAGAGAAA CATCTGCAAA CTTTTCTGAT GTCTATTTGC    3840

ACCTGCAAAT GCGGACGTCT TAGTACATGC CATCGGAACT CTGTCTAGGG AAGTACAAAT    3900

GTCTTTTCGA ATGTTATCGG TAAGCTGTCT TCTCCCGAGT TCCCCGAATG AAAATATCAT    3960

GAAAACACTG TCAAAGCCAC ACGAGTCCAA AGATTCTACA TCTTCGGTGT TATTCGTTTT    4020

GACATGCCCT TGGACGGCTA CGTCTTTTGC GTGGTCCGGA GTAACATGAG AATGCGTATC    4080

ATGACATTCG TACGATCCGG AAACACAGTC AATAGACGAG GCTCCATATA GAACTTCTGT    4140

CACAGAGGGG ATCTCGGTAC C                                              4161
```

RECOMBINANT LIVE AVIAN VACCINE, USING AS VECTOR THE AVIAN INFECTIOUS LARYNGOTRACHEITIS VIRUS

This application claims priority from French application number 96 15687, filed Dec. 16, 1996, incorporated herein by reference.

The present invention relates to vaccines for avian used based on infectious laryngotracheitis virus (ILTV), into which at least one heterologous nucleotide sequence, in particular coding for and expressing an antigenic polypeptide of an avian pathogenic agent, has been inserted by genetic recombination under conditions providing for an immunization leading to an effective protection of the vaccinated animal against the said pathogenic agent.

The infectious laryngotracheitis virus (ILTV) is an alpha-herpes virus (B. Roizman, *Arch. Virol.* 1992. 123. 425–449) which causes a serious respiratory pathology (infectious laryngotracheitis or ILT) in chickens (L. E. Hanson and T. J. Bagust, *Diseases of Poultry* 9th edn 1991. pp 485–495. Ames, Iowa State University Press). The vaccines currently available against this illness contain an attenuated strain which can be administered via different routes, including the intranasal, conjunctival and cloacal routes, in the drinking water and by aerosol (L. E. Hanson and T. J. Bagust, *Diseases of Poultry* 9th Edition 1991. pp 485–495. Ames, Iowa State University Press).

Molecular biology studies of the ILTV virus have enabled the viral genome to be characterized (M. A. Johnson et al., *Arch. Virol.* 1991. 119. 181–198) and a few genes of the virus to be identified (A. M. Griffin, *J. Gen. Virol.* 1989. 70. 3085–3089), including the genes coding for thymidine kinase (UL23) (A. M. Griffin and M. E. G. Boursnell, *J. Gen. Virol.* 1990. 71. 841–850; C. L. Keeler et al., *Avian Dis.* 1991. 35. 920–929), the glycoprotein gB (UL27) (A. M. Griffin, *J. Gen. Virol.* 1991. 72. 393–398; K. Kongsuwan et al., *Virology* 1991. 184. 404–410; D. J. Poulsen et al., *Virus Genes* 1991. 5. 335–347), the glycoprotein gC (UL44) (D. H. Kingsley et al., *Virology* 1994. 203. 336–343), the p40 capsid protein (UL26) (A. M. Griffin, *Nucl. Acids Res.* 1990. 18. 3664), the protein homologous to the herpes simplex (HSV-1) protein ICP4 (M. A. Johnson et al., *Virus Research* 1995. 35. 193–204), the proteins homologous to the HSV-1 proteins ICP27 (UL54), glycoprotein gK (UL53) and DNA helicase (UL52) (M. A. Johnson et al., *Arch. Virol.* 1995. 140. 623–634), ribonucleotide reductase (A. M. Griffin, *J. Gen. Virol.* 1989. 70. 3085–3089, WO-A-90/02802), the genes UL1 to UL5 (W. Fuchs and T. C. Mettentleiter, *J. Gen. Virol.* 1996. 77. 2221–2229), and the genes present in the short unique sequence of the genome ($U_S$) (M. A. Johnson et al., *DNA Sequence—The Journal of Sequencing and Mapping* 1995. Vol. 5. pp 191–194; K. Kongsuwan et al., *Arch. Virol.* 1995. 140. 27–39; K. Kongsuwan et al., *Virus Research* 1993. 29. 125–140; K. Kongsuwan et al., *Virus Gene* 1993. 7. 297–303; M. A. Wild et al., *Virus Genes* 1996. 12. 107–116; WO-A-92/03554; WO-A-95/08622.

An objective of the present invention is to develop an avian vaccine based on recombinant ILTV virus expressing a heterologous gene, this virus being capable of replication and of including an immunity in the vaccinated host while retaining the property of being perfectly harmless.

Another objective of the invention is to provide such a vaccine which is, at the same time, especially effective against infectious laryngotracheitis (ILT).

Another objective of the invention is to provide such a vaccine which can be used in mass vaccination via the mucosal route, for example by means of an aerosol or in the drinking water, such that the replication of the virus in the mucosae enables a mucosal and systemic immunity to be induced. Such a Mucosal immunity will be especially effective for combating respiratory diseases, and also against other diseases for which the route of entry of the pathogenic agent is mucosal.

Another objective of the invention is to provide such a vaccine which can be used both in adults and in young animals.

A specific objective is to provide such a vaccine which can be used in mass vaccination via the mucosal route of very young animals such as one-day-old chicks.

Another objective of the invention is to provide a vaccine against ILT which has an enhanced efficacy relative to the parent strain and which might even possibly permit the insertion and expression of a heterologous gene.

In the course of their work on the ILTV virus, the inventors found a genomic region which proved entirely suitable as a site for insertion of heterologous genes. This made it possible to develop a recombinant live vaccine based on an ILTV vector into which is inserted at least one sequence coding for an avian immunogen, especially the protein HN and F of the Newcastle disease virus (NDV), and/or the glycoprotein gB of the Marek's disease virus (MDV), and/or the protein VP2 of the Gumboro disease virus (IBDV), and/or the proteins S and M of the infectious bronchitis virus (IBV). Such a vaccine incorporating a sequence coding NDV, MDV and/or IBV proteins provides for a satisfactory protection of the animals against Newcastle disease, against Marek's disease, against Gumboro disease and against infectious bronchitis, respectively.

Hence a subject of the present invention is a recombinant live avian vaccine comprising as vector the ILTV virus comprising at least one heterologous nucleotide sequence, in particular coding for and expressing an antigenic polypeptide of an avian pathogenic agent, inserted into the insertion locus formed by the intergenic region located between the stop codons of ORF B and ORF C of the ILTV virus, which region, in a particular ILTV strain, is defined between nucleotides 908 and 994 in the sequence SEQ ID NO:1.

While the particular sequence described in the application (SEQ ID NO:1) originates from the vaccinal strain of ILTV T-20 Dec. 8, 1966 (LT BLEN vaccine) obtained from select Laboratories (10026 Main Street P.O. Box 6, Berlin, Md. 21811, USA), it is quite obvious that a person skilled in the art will be able to use the other strains of ILTV, bearing in mind the information given in the present document regarding the vaccinal strain.

ORF B and ORF C correspond, respectively, to the UL3.5 and UL4 genes described in the paper by W. Fuchs and T. C. Mettenleiter (*J. Gen. Virol.* 1996. 77. 2221–2229) of a pathogenic strain obtained from D. Lütticken, Boxmeer, Holland. This paper in no way suggests that this intergenic region might be used as insertion locus.

The sequence referenced SEQ ID NO:19 reproduces, for this pathogenic strain, the sequence equivalent to SEQ ID NO:1. The intergenic region used as insertion locus in accordance with the invention is included in SEQ ID NO:19 between nucleotides 908 and 994.

Heterologous sequence is understood to mean a sequence which does not originate from this insertion locus, that is to say either a sequence whose source is not the ILTV virus or a sequence originating from another genomic region of this virus, or alternatively originating from another ILTV strain, in particular a virulent strain.

Insertion into the insertion region is understood, in particular, to mean simple insertion or insertion after total or partial deletion of the insertion locus.

It is possible to inert one or more expression cassettes each comprising at least one sequence to be expressed.

To express the inserted sequence, it is preferable to use a strong eukaryotic promoter such as the CMV immediate early (IE) promoter, the Rous sarcoma virus (RSV) LTR and the SV40 virus early promoter, CMV immediate early (IE) promoter is understood, in particular, to mean the fragment given in the examples as well as its subfragments that retain the same promoter activity. The CMV IE promoter can be the human promoter (HCMV IE) or the murine promoter (MCMV IE), or alternatively a CMV IE promoter of another origin, for example of monkey, rat, guinea pig or porcine origin.

Other promoters of viral or cellular origin may also be used.

Among promoters of viral origin, there may also be mentioned the promoters of genes of the ILTV virus (genes considered to be immediate early (ICP4, ICP27, etc.), early (thymidine kinase, DNA helicase, ribonucleotide reductase, etc.) or late (gB, gD, gC, gK, etc.)), of the Marek's disease virus (MDV), (gB, gC, pp38, pp14, ICP4, Meq, etc., genes) or of the herpes virus of turkeys (gB, gC, ICP4, etc., genes).

The nucleotide sequence inserted into the ILTV vector in order to be expressed can be any sequence coding for an antigenic polypeptide of an avian pathogenic agent, capable, when expressed under the favourable conditions brought about by the invention, of providing for an immunization leading to an effective protection of the vaccinated animal against the pathogenic agent. The nucleotide sequences coding for the antigens of interest for a given disease may hence be inserted under the conditions of the invention.

This nucleotide sequence inserted into the ILTV vector may also code for an immunomodulatory polypeptide, and in particular a cytokine.

As a noteworthy feature, the vaccines according to the invention may be used for the in ovo vaccination of one-day-old or older chicks and of adults. Different administration routes may be used: the parenteral route, or the mucosal routes such as the oronasal (drinking water, aerosol), conjunctival (drop in the eye) or cloacal route, with a preference for the routes permitting a mucosal mass vaccination (drinking water, aerosol).

The invention proves especially useful both for protection against respiratory pathologies and against systemic pathologies, by blocking the natural routes of entry of the pathogenic agent.

The invention may, in particular, be used for the insertion of a nucleotide sequence coding appropriately for an antigenic protein of the NDV virus, and especially the glycoprotein HN or the glycoprotein F. A recombinant live vaccine is thereby obtained affording, in addition to protection against infectious laryngotracheitis, a satisfactory protection against Newcastle disease.

The recombinant vaccine against Newcastle disease will preferably contain from 10 to $10^4$ pfu/dose.

Other preferred cases of the invention are the insertion of nucleotide sequences coding for antigens of other avian pathogenic agents, and in particular, but without implied limitation, antigens of the Marek's disease virus, especially gB, gC, gD and gH+gL genes (WO-A-90/02803), of the Gumboro disease virus, especially VP2 gene, of the infectious bronchitis virus (IBV), especially S and M genes (M. Binns et al., *J. Gen. Virol.* 1985. 66. 719–726; M. Boursnell et al., *Virus Research* 1984. 1. 303–313), of the chicken anaemia virus (CAV), especially VP1 (52 kDa)+VP2 (24 kDa) (N. H. M. Noteborn et al., *J. Virol.* 1991. 65. 3131–3139), of the ILTV virus, especially the genes coding for gB (A. M. Griffin, *J. Gen. Virol.* 1991. 72. 393–398), or for gD (M. A. Johnson et al., *DNA Sequence—The Journal of Sequencing and Mapping* 1995. Vol. 5. pp 191–194. Harwood Academic Publishers GmbH) or for gp60 (K. K. Kongsuwan et al., *Virus Genes* 1993. 7. 297–303) and of the virus of infectious swollen head syndrome (or chicken pneumovirosis or turkey rhinotracheitis virus (TRTV); pneumovirus), especially the fusion glycoprotein F (Q. Yu et al., *J. Gen Virol.* 1991. 72. 75–81) or the attachment glycoprotein G (R. Ling et al., *J. Gen. Virol.* 1991. 73. 1709–1715; K. Juhasz and J. Easton, *J. Gen. Virol.* 1994. 75 2873–2880). The doses were preferably the same as those for the Newcastle vaccine.

In the context of the present invention, it is naturally possible to insert more than one heterologous sequence into the said ILTV virus, in particular in this locus. It is possible, in particular, to insert therein sequences originating from the same virus or from different viruses, which also comprises the insertion of ILTV sequences and sequences from another avian virus. It is also possible to ally therewith sequences coding for immunomodulators, and especially cytokines.

For example, the CMV IE promoter is allied with another promoter so that their 5' ends are adjacent (implying transcriptions in opposite directions), which enables two nucleotide sequences, one under the control of the CMV IE promoter and the other under that of the allied promoter, to be inserted into the insertion zone. This construction is noteworthy for the fact that the presence of the CMV IE promoter, and in particular of its activating (enhancer) portion, activates the transcription induced by the allied promoter. The allied promoter can be, in particular, a promoter of a gene of the ILTV virus or of the MDV or HVT virus.

An advantageous case of the invention is a vaccine comprising a nucleotide sequence coding for NDV HN and a nucleotide sequence coding for NDV F or an antigen of another avian disease, in particular the ones mentioned above, one of the genes being under the control of the CMV IE promoter and the other under the control of the allied promoter.

It is also possible to introduce two CMV IE promoters of different origins with their 5' ends adjacent.

The expression of several heterologous genes inserted into the insertion locus may also be made possible by insertion between the open reading frames of these genes of a sequence known as "IRES" (internal ribosome entry site) originating, in particular, from a picornavirus such as the swine vesicular disease virus (SVDV; B. -F Chen et al., *J. Virology,* 1993, 67, 2142–2148), the encephalomyocarditis virus (EMCV; R. J. Kaufman et al., *Nucleic Acids Research,* 1991. 19, 4485–4490), the aphthous fever virus (FMDV; N. Luz and E. Beck. *J. Virology,* 1991, 65, 6486–6494), or alternatively from another origin. The content of the 3 papers cited is incorporated by reference. The cassette for expression of two genes would hence have the following minimum structure: promoter—gene 1—IRES—gene 2—polyadenylation signal. The recombinant live vaccine according to the invention may hence comprise, inserted into the insertion locus, an expression cassette comprising in succession a promoter, two or more genes separated pairwise by an IRES, and a polyadenylation signal.

In addition to the insertion into the locus according to the invention, it is possible to carry out one or more other insertions, one or more mutations or one or more deletions elsewhere in the genome; if the parent strain is virulent, it is possible, for example, to inactivate (by deletion, insertion or mutation) genes involved in the virulence, such as the thymidine kinase gene, the ribonucleotide reductase gene, the gE gene, etc. In any case, the insertion into a locus other than the one described in the invention enables other genes to be expressed.

A subject of the present invention is also a vaccine against ILT, comprising a recombinant ILTV virus into which an exogenous promoter, especially a strong promoter as described above, has been inserted upstream of the genes coding for major immunogens of ILTV, preferably the genes coding for gB (A. M. Griffin, *J. Gen. Virol.* 1991. 72, 393–398) or for gD (M. A. Johnson et al., *DNA Sequence—The Journal of Sequencing and Mapping* 1995. Vol. 5. pp 191–194. Harwood Academic Publishers GmbH) or for gp60 (K. K. Kongsuwan et al., *Virus Genes* 1993. 7. 297–303). This enables the level of expression of one or more of these genes to be increased, and thus makes it possible to produce a vaccine having enhanced efficacy against ILT. This may, of course, be combined with a construction as described above comprising the insertion of a heterologous sequence into the insertion locus.

A subject of the present invention is also a multivalent vaccine formula comprising, as a mixture or to be mixed, a vaccine as defined above with another vaccine, and in particular another recombinant live avian vaccine as defined above, these vaccines comprising different inserted sequences, in particular from different pathogens.

A subject of the present invention is also a method for preparing the vaccines according to the invention, as emerges from the description.

A subject of the present invention is also a method of avian vaccination, comprising the administration of a recombinant live vaccine or of a multivalent vaccine formula as defined above. Its subject is, in particular, such a method for the vaccination in ovo of one-day-old or older chicks and of adults. Different routes of administration of the vaccine may be used (see above), with a preference for the routes permitting a mass vaccination via the mucosal route (aerosol, drinking water), the dose of vaccine preferably being selected between $10^1$ and $10^4$ per animal.

A subject of the present invention is also an ILTV virus comprising at least one heterologous nucleotide sequence as described above, inserted into the insertion locus as defined above.

A subject of the present invention is also all or part of the sequence SEQ ID NO:1; parts of this sequence are understood not only to mean the characterized ORFs taken separately or their fragments, but also the intergenic region located between ORF B and ORF C and the fragments located on each side of this intergenic region, which can, where appropriate, include a part of this intergenic region and which may serve as flanking arms for a homologous recombination, a technique which is, moreover, perfectly well known to a person skilled in the art. Generally speaking, but without implied limitation, the flanking arms can have from 100 to 1500 base pairs.

The invention will now be described in greater detail by means of the non-limiting examples of implementation, taken with reference to the drawing, wherein:

FIG. 1: Restriction map of the cloned fragment and position of the ORFs

FIG. 2: Sequence of 4161 bp and translation of ORFs A, B, C and D of the Select Laboratories vaccinal strain T-20

FIG. 3: Scheme for obtaining the plasmid pEL157

FIG. 4: Scheme for obtaining the plasmid pEL024

FIG. 5: Scheme for obtaining the plasmid pEL027

FIG. 6: Diagram of the plasmid pEL158

FIG. 7: Scheme for obtaining the plasmid pCD009

FIG. 8: Scheme for obtaining the plasmid pEL070

FIG. 9: Diagram of the plasmid pEL159

FIG. 10: Sequence of the NDV HN gene

FIG. 11: Scheme for obtaining the plasmid pEL030

FIG. 12: Diagram of the plasmid pEL160

FIG. 13: Diagram of the plasmid pEL033

FIG. 14: Diagram of the plasmid pEL161

FIG. 15: Diagram of double expression cassette

FIG. 16: Diagram of the plasmid pCD011

FIG. 17: Diagram of the plasmid pEL163

FIG. 18: Sequence of 4161 bp and translation of UL3, 3.5, 4 and 5 of Lütticken's pathogenic strain

SEQUENCE LISTING

SEQ ID NO:1 Sequence of the KpnI—KpnI fragment (4161 bp, see FIG. 2)

SEQ ID NO:2 Oligonucleotide EL001

SEQ ID NO:3 Oligonucleotide EL002

SEQ ID NO:4 Oligonucleotide EL003

SEQ ID NO:5 Oligonucleotide EL004

SEQ ID NO:6 Oligonucleotide MB070

SEQ ID NO:7 Oligonucleotide MB071

SEQ ID NO:8 Sequence of the NDV NH gene (see FIG. 10)

SEQ ID NO:9 Oligonucleotide EL071

SEQ ID NO:10 Oligonucleotide EL073

SEQ ID NO:11 Oligonucleotide EL074

SEQ ID NO:12 Oligonucleotide EL075

SEQ ID NO:13 Oligonucleotide EL076

SEQ ID NO:14 Oligonucleotide EL077

SEQ ID NO:15 Oligonucleotide CD001

SEQ ID NO:16 Oligonucleotide CD002

SEQ ID NO:17 Oligonucleotide CD003

SEQ ID NO:18 Oligonucleotide CD004

SEQ ID NO:19 Sequence of the KpnI—KpnI fragment (4161 bp, see FIG. 18)

EXAMPLES

All the plasmid constructions were carried out using the standard techniques of molecular biology described by Sambrook J et al. (*Molecular Cloning: A Laboratory Manual.* 2nd Edition. Cold Spring Harbor Laboratory. Cold Spring Harbor. N.Y. 1989). All the restriction fragments used for the present invention were isolated using the "Geneclean" kit (BIO101 Inc. La Jolla, Calif.).

The virus used as parent virus may be selected from the vaccinal strains described in J. R. Andreasen et al. (*Avian Diseases* 1990. 34. 646–656) or the strain T-20 Dec. 8, 1966 obtained from Select Laboratories 10026 Main Street P.O. Box 6 Berlin, Md. 21811, USA. It is also possible to use virulent strains such as Lütticken's strain (see above), the strain N-71851 (ATCC VR-783) or the strain 83-2 from USDA, which may be attenuated by known techniques, for example the one described in WO-A-95/08622.

Example 1

Culture of the ILTV virus:

The ILTV virus (Select Laboratories strain T20) is cultured on primary chicken kidney cells (CKC); these cells are cultured in MEM medium supplemented with 3% of foetal calf serum (FCS) in 75 $cm^2$ culture flasks ($2\times10^5$ cells/$cm^2$) one or two days before inoculation.

On the day of inoculation, a flask of 1000 doses of lyophilized vaccine is resuspended in 10 ml of MEM medium supplemented with 1% of FCS; approximately 0.5 ml of this solution is then applied to the CKC culture. Next day, the medium is changed, and the day after, when the cytopathogenic effect (CPE) becomes generalized, the culture flasks are frozen at −70° C.

Culture of the ILTV virus may also be carried out on immortalized chicken liver cells, and in particular on the LMH line (W. M. Schnitzlein et al., *Avian Diseases* 1994. 38. 211–217).

Example 2

Preparation of ILTV genomic DNA:

After 2 cycles of freezing/thawing, the ILTV culture (two 75 cm² flasks) is harvested and centrifuged at low speed (5000 rpm in a 20 rotor, Beckman JA21 centrifuge, for 5 minutes) to remove large cell debris. The supernatant is ultracentrifuged (100,000 rpm, TLA100.3 rotor, Beckman TL100 centrifuge, for 1 hour). The pellet is then taken up in 1.6 ml of TEN-SDS (10 mM Tris pH 8.0; 1 mm EDTA; 0.5 NaCl; 0.5% sodium dodecyl sulphate), and 35 $\mu$l of a 20 mg/ml proteinase K solution are then added; the solution is incubated for 3 to 4 hours on a waterbath at 37° C., and the DNA is then extracted 3 times with phenol/chloroform and once with chloroform and is then precipitated with ethanol at −20° C. After centrifugation, the pellet is rinsed with 70% ethanol, dried and resuspended in 200 $\mu$l of TE (10 mM Tris pH 8.0; 1 mM EDTA). The nucleic acid concentration is then assayed in a spectrophotometer ($OD_{260}$). The DNA may be digested directly with the appropriate restriction enzymes and then cloned into the plasmid pBluescript II SK+; similarly, it may also be used in transfection experiments for obtaining a recombinant virus.

Example 3

Isolation and purification of recombinant ILTV virus:

The donor plasmid composed of a cassette for the expression of a polypeptide inserted between two flanking regions of the insertion locus is digested with a restriction enzyme permitting linearization of the plasmid, and it is then extracted with a phenol/chloroform mixture, precipitation with absolute ethanol and taken up in sterile water. 24-Hour primary CKC cells are then transfected with the following mixture: 0.2 to 1 $\mu$g of linearized donor plasmid+2 to 5 $\mu$g of ILTV viral DNA (prepared as in Example 2) in 300 $\mu$l of OptiMEM medium (Gibco BRI Cat # 041-01985H) and 100 $\mu$g of LipofectAMINE diluted in 300 $\mu$l of medium (final volume of the mixture=600 $\mu$l. These 600 $\mu$l are then diluted in 3 ml (final volume) of medium and plated out on $5\times10^6$ CKC. The mixture is left in contact with the cells for 5 hours, then removed and replaced by 5 ml of culture medium. The cells are then left in culture for 3 to 8 days at +37° C. and thereafter, when the cytopathogenic effect has become apparent, they are frozen at −70° C. After thawing and, where appropriate, sonication, this viral population is cloned at limiting dilution in microplates (96-well) in order to isolate a homogeneous population of recombinant virus. These plates are left in culture for 1 to 3 days, and the supernatant is then harvested in an empty 96-well plate and the plate containing the supernatants is placed at 4° C. or at −70° C. The cells remaining in the other plates are then fixed with 95% acetone for 20 to 30 minutes at 20° C., or for 5 minutes at room temperature. An indirect immunofluorescence (IIF) reaction is carried out with a monoclonal antibody directed against the polypeptide expressed in order to look for plaques expressing this polypeptide. A further cloning is then performed in the same manner (at limiting dilution in 96-well plates) from the supernatant present in the wells of the plates placed at 4° C. or at −70° C. and corresponding to the wells displaying positive plaques in IIF. In general, 4 successive isolation cycles (limiting dilution, harvesting of the supernatant, cell monitoring by IIF, limiting dilution from the supernatant, etc.) suffice to obtain recombinant viruses all of whose progeny display a specific fluorescence. The genomic DNA of these recombinant viruses is characterized at molecular level by conventional PCR and Southern blot techniques using the appropriate oligonucleotides and DNA probes.

The isolation of recombinant virus may also be carried out by hybridization with a probe specific for the inserted expression cassette. For this purpose, the viral population harvested after transfection is diluted and applied to CKC cells (cultured in Petri dishes) so as to obtain isolated plaques. After 1 hour of contact at 37° C., the infection medium is removed and replaced by 5 ml of MEM medium containing 1% of agarose, kept supercooled at 42° C. When the agarose has solidified, the dishes are incubated for 48 to 72 hours at 37° C. in a $CO_2$ incubator until plaques have appeared. The agarose layer is then removed and a transfer of viral plaques is carried out on a sterile nitrocellulose membrane of the same diameter as the Petri dish used for culturing. This membrane is itself transferred onto another nitrocellulose membrane so as to obtain a reverse "copy" of the first transfer. The plaques transferred onto the latter copy are then hybridized according to the standard techniques known to the person skilled in the art with a digoxigenin-labelled DNA fragment (DNA Labelling Kit, Boehringer Mannheim, CAT # 1175033) of the expression cassette. After hybridization, washes and placing in contact with the visualization substrate, the nitrocellulose membrane is placed in contact with an autoradiographic film. The positive hybridization images on this membrane indicate which plaques are the ones containing recombinant ILTV viruses which have inserted the expression cassette. The plaques corresponding to these positive plaques are cut out under sterile conditions from the first nitrocellulose membrane, placed in an Eppendorf tube containing 0.5 ml of MEM medium and sonicated to release the virions from the membrane. The medium containing the Eppendorf tube is then diluted in MEM medium, and the dilutions thereby obtained are used to infect further cultures of CKC cells.

Example 4

Cloning and characterization of an ILTV genomic region:

The DNA extracted from the ILTV virus was digested with restriction enzyme KpnI for 2 hours at 37° C. The restriction enzyme was then removed by a phenol/chloroform extraction followed by an ethanol precipitation. The fragments resulting from this digestion were then ligated (overnight at 14° C.) with the plasmid pBluescript II Sk+ (pBS-SK+; Stratagene) digested with KpnI and treated with alkaline phosphatase; analysis of the clones obtained after transformation of *E. coli* DHA5α bacteria and culture on dishes of ampicillin-supplemented medium enables KpnI—KpnI inserts of different sizes to be identified, including a fragment of approximately 4.2 kb (plasmid pEL112).

Complete sequencing of the insert present in pEL112 (see FIG. 1) enabled two complete open reading frames (ORFs) (ORF B and ORF C) and a large part of two other ORFs (ORF A an ORF D) to be revealed. The restriction map of this cloned and sequenced genomic region is shown in FIG. 1; the sequence of 4161 bp (SEQ ID NO:1) is shown in FIG. 2. The position and the amino acid sequence of ORFs A, B, C and D are also shown in FIGS. 1 and 2, respectively.

The sequence between the stop codons of ORFs B and C (position from 908 to 994 on SEQ ID NO;1) can be used to insert cassettes for the expression of polypeptides into the ILTV genome. This sequence is referred to as the insertion locus. The insertion may take place with or without deletion in the intergenic region (see Example 5).

Example 5

Construction of the donor plasmid pEL157 for insertion into the intergenic region between ORFs B and C:

The plasmid pEL112 (7116 bp) was digested with the enzymes NotI and SpeI to isolate the 4.5-kb NotI-SpeI fragment. The fragment thus digested was then treated with the DNA polymerase (Klenow fragment) in the presence of dNTP in order to make the ends blunt; after ligation and transformation of E. coli bacteria, the clone pEL156 (4503 bp) was obtained.

The oligonucleotides EL001 (SEQ ID NO:2) and EL002 (SEQ ID NO:3) were used as primer for a first chain amplification by Taq polymerase (PCR). The oligonucleotides EL003 (SEQ ID NO:4) and EL004 (SEQ ID NO:5) were used as primer for a second chain amplification by Taq polymerase (PCR).

EL001 (SEQ ID NO:2): 5' TATTGCTTTCTAC-CGAAGTCGG 3'

EL002 (SEQ ID NO:3): 5' ACGCGAATTCAAATAC-GAGCATTTAATTATTGCG 3'

EL003 (SEQ ID NO:4): 5' TCTCCAGAATCGCTG-GAGTGTCC 3'

EL004 (SEQ ID NO:5): 5' TGCGCGAATTCG-TAAGCTTTGATATCCAGTCGACA TAATTTGGT-GTTTATTACTTTTA 3'

The PCRs were performed in the presence of PCR buffer, dNTP, plasmid pEL156 DNA, Taq polymerase and, for the first PCR, the oligonucleotides EL001 and EL002, and for the second PCR, the oligonucleotides EL003 and EL004.

For both PCRs, 25 cycles were performed (30 seconds at 94° C.; 30 seconds at 60° C. and 30 seconds at 72° C.). The products of both PCRs were purified by a phenol/chloroform extraction followed by a purification with ethanol. The product of the first PCR (EL001/EL002) was then digested with the restriction enzymes XbaI and EcoRI for 2 h at 37° C. to give a 120-bp XbaI-EcoRI DNA fragment which was eluted after agarose gel electrophoresis. The product of the second PCR (EL003/EL004) was then digested with the restriction enzymes XhoI and EcoRI for 2 h at 37° C. to give an 85-bp XhoI-EcoRI DNA fragment which was eluted after agarose gel electrophoresis. Plasmid pEL156 was digested with the enzymes XbaI and XhoI. The two PCR fragments, XbaI and EcoRI (120 bp) and XhoI-EcoRI (85 bp), were ligated overnight at 14° C. with plasmid pEL156 digested with XbaI and XhoI. After transformation of E. coli bacteria and culture on dishes of ampicillin-supplemented medium, the clone pEL157 (4531 bp), comprising an EcoRI-HindIII-EcoRV-SalI polylinker, was obtained (see scheme for obtaining pEL157 in FIG. 3).

Example 6

Figure 4:
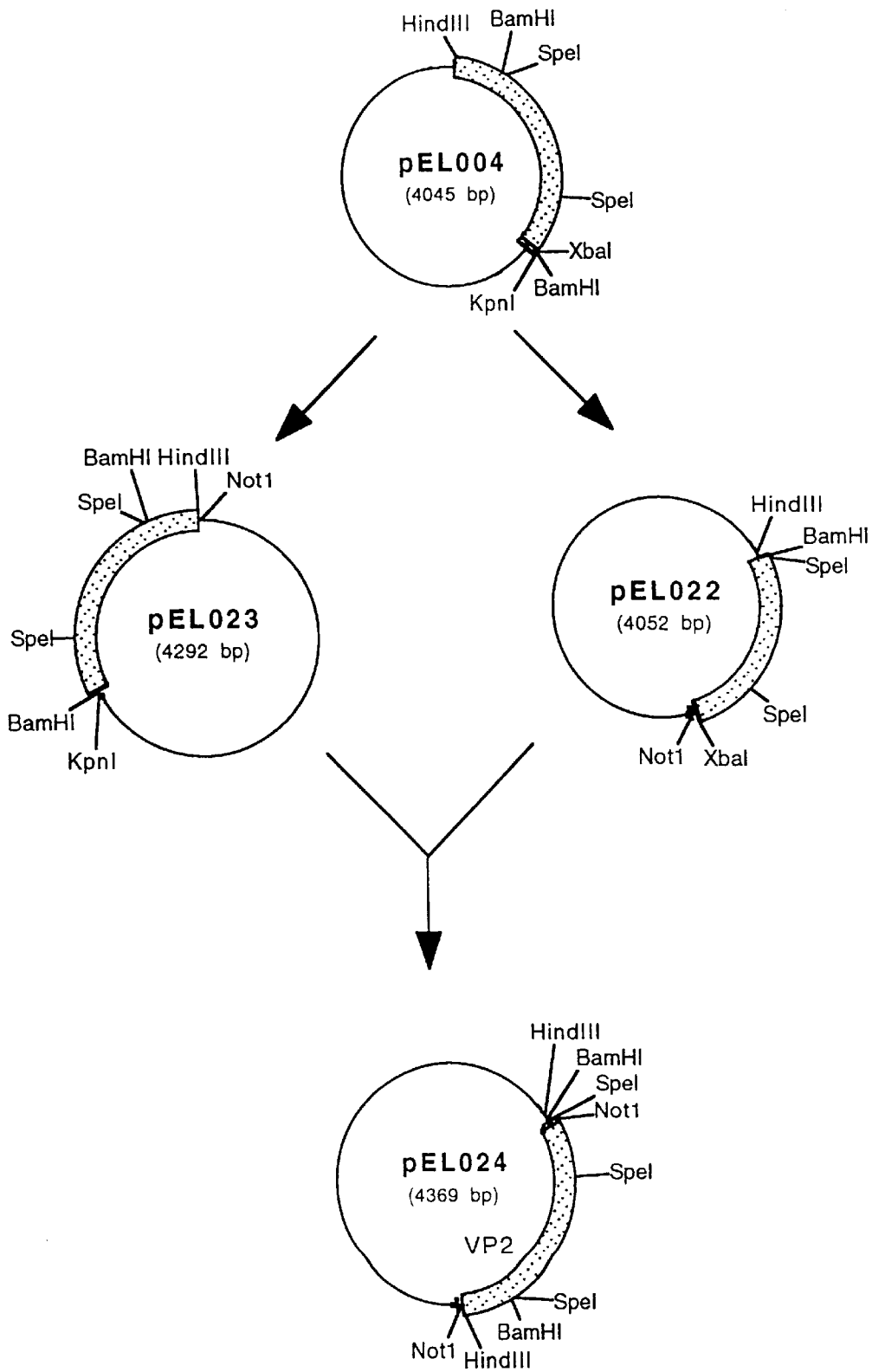

Construction of the donor plasmid pEL158 for the insertion of a cassette for the expression of the IBDV VP2 gene under the control of the HCMV IE promoter into the intergenic site between ORFs B and C, and isolation of vILTV8:

6.1—Cloning of the Gumboro disease virus (IBDV) VP2 gene and construction of a cassette for the expression of VP2 under the control of the HCMV IE promoter The plasmid pEL004 (see FIG. 4;=plasmid pGH004 described in French Patent Application 92/13109) containing the IBDV VP2 gene in the form of a BamHI-HindIII cassette was digested with BamHI and XbaI to isolate the 1104-bp BamHI-XBAI fragment (truncated VP2 gene). This fragment was cloned into the vector pBS-SK+ previously digested with XbaI and BamHI to give the plasmid pEL022 of 4052 bp (FIG. 4). The vector pBS-SK+ was digested with EcoRV and XbaI and then ligated with itself to give pBS-SK+ (modified). Plasmid pEL004 was digested with KpnI and HindIII to isolate the 1387-bp KpnI-HindIII fragment containing the complete IBDV VP2 gene. This fragment was cloned into the vector pBS-SK+ previously digested with KpnI and HindIII to give the plasmid pEL023 of 4292 bp (FIG. 4). Plasmid pEL022 was digested with BamHI and NotI to isolate the 1122-bp BamHI-NotI fragment (fragment NotI). Plasmid pEL023 was digested with BamHI and NotI to isolate the 333-bp BamHI-NotI fragment (fragment B). The fragments A and B were ligated together with the vector pBS-SK+ previously digested with NotI and treated with alkaline phosphatase to give plasmid pEL024 of 4369 bp (FIG. 4).

Figure 5:
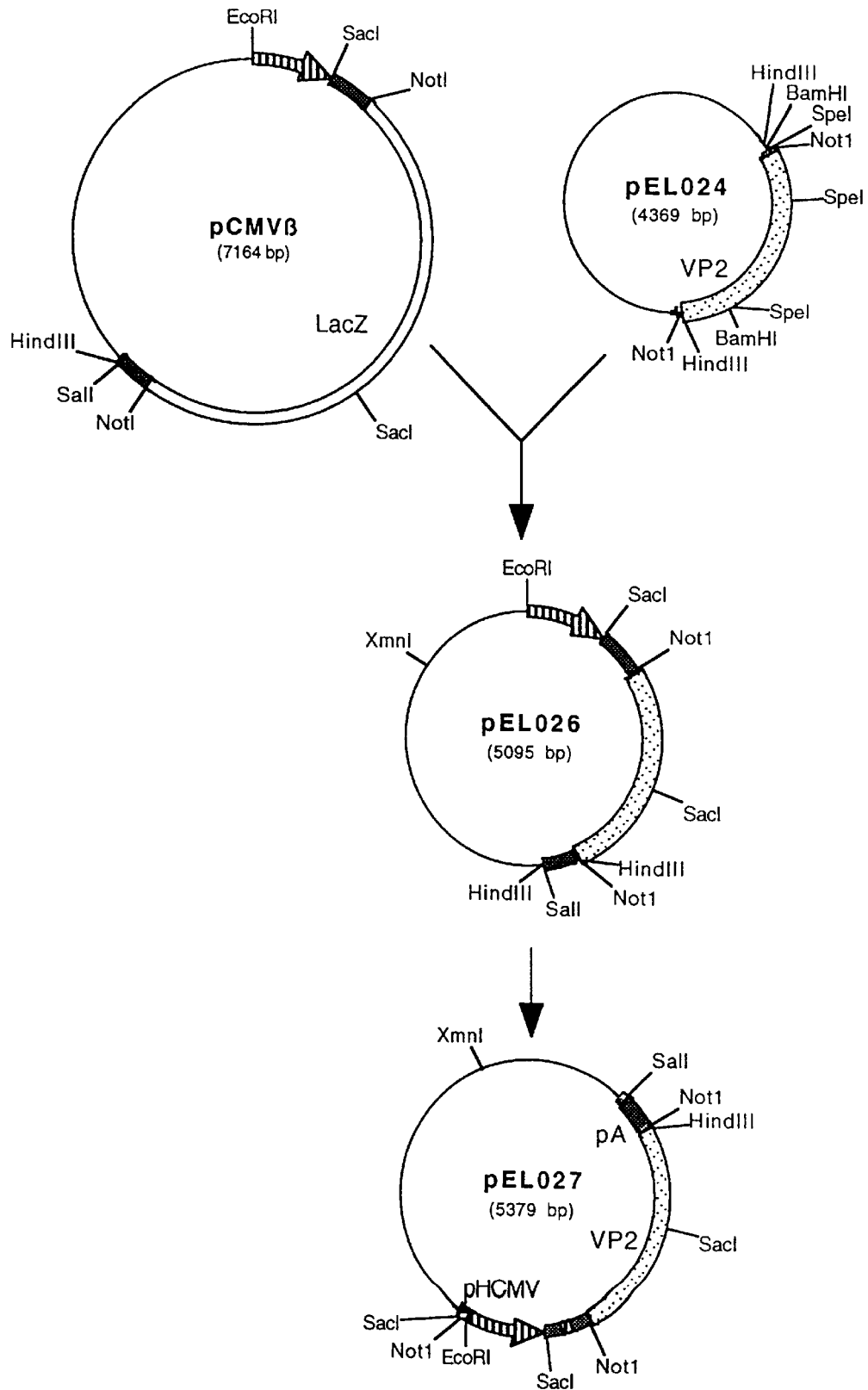

Plasmid pEL024 was digested with NotI to isolate the 1445 bp NotI-NotI fragment. This fragment was ligated with the plasmic pCMVβ (Clontech Cat # 6177-1, FIG. 5) previously digested with NotI to give the plasmid pEL026 of 5095 bp (FIG. 5).

Plasmid pEL026 was digested with EcoRI, SalI and XmnI to isolate the 2428 bp EcoRI-SalI fragment. This fragment was ligated with the vector pBS-SK+ previously digested with EcoRI and SalI to give plasmid pEL027 of 5379 bp (FIG. 5).

6.2—Construction of the donor plasmid pEL158

Figure 6:
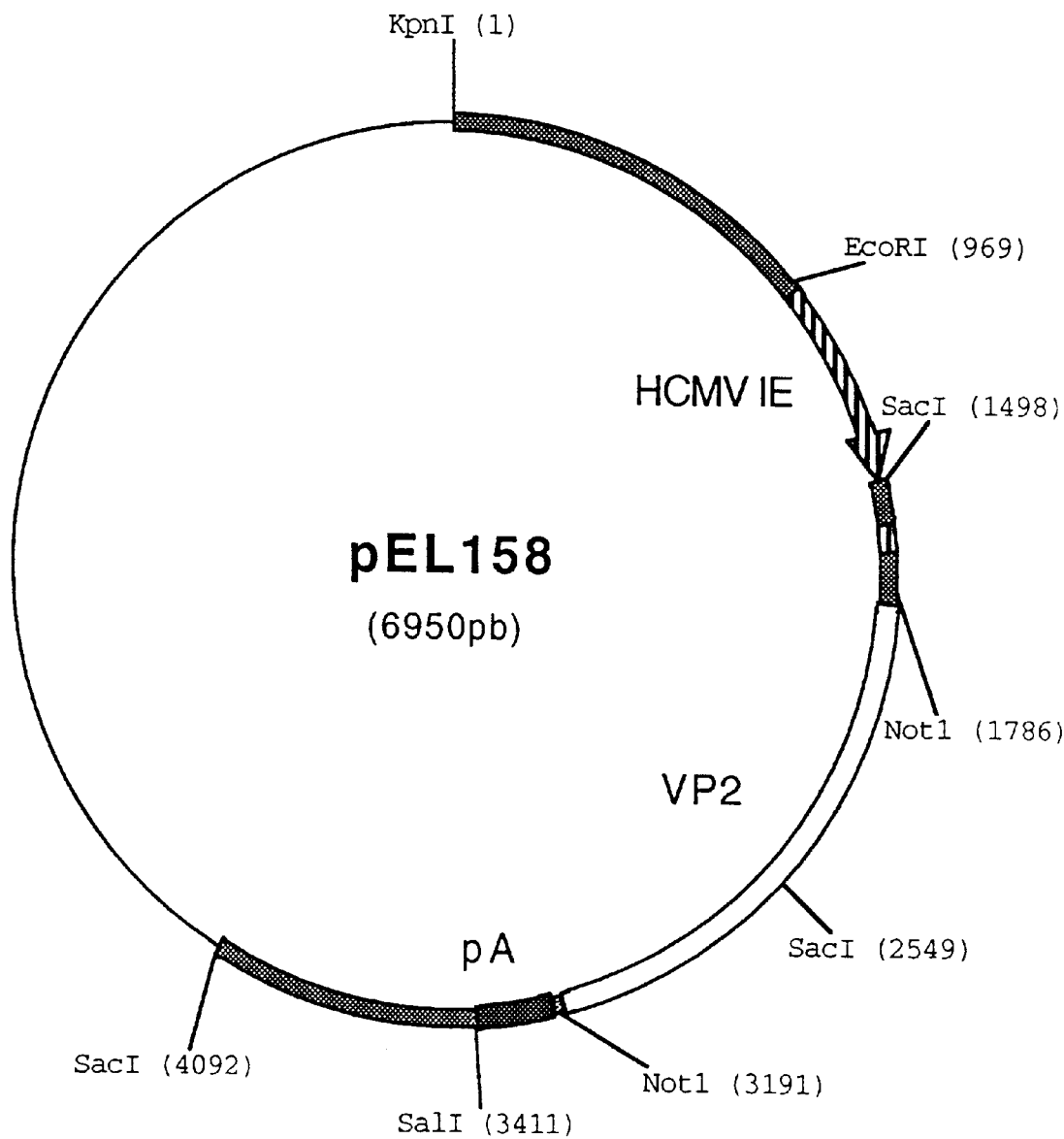

Plasmid pEL027 was digested with EcoRI, SalI and XmnI to isolate the 2428 bp EcoRI-SalI fragment. This fragment was ligated into plasmid pEL157 (see Example 5 and FIG. 3) previously digested with EcoRI an SalI to give plasmid pEL158 of 6950 bp (FIG. 6).

6.3—Isolation and purification of the recombinant virus vILTV8

The virus VILTV8 was isolated and purified after cotransfection of plasmid pEL158 DNA previously linearized with the enzyme KpnI and the viral DNA, as described in Example 3. This recombinant contains an HCMV-IE/IBDV VP2 cassette in the intergenic site between ORFs B and C of the ILTV virus (see Example 5).

Example 7

Figure 7:
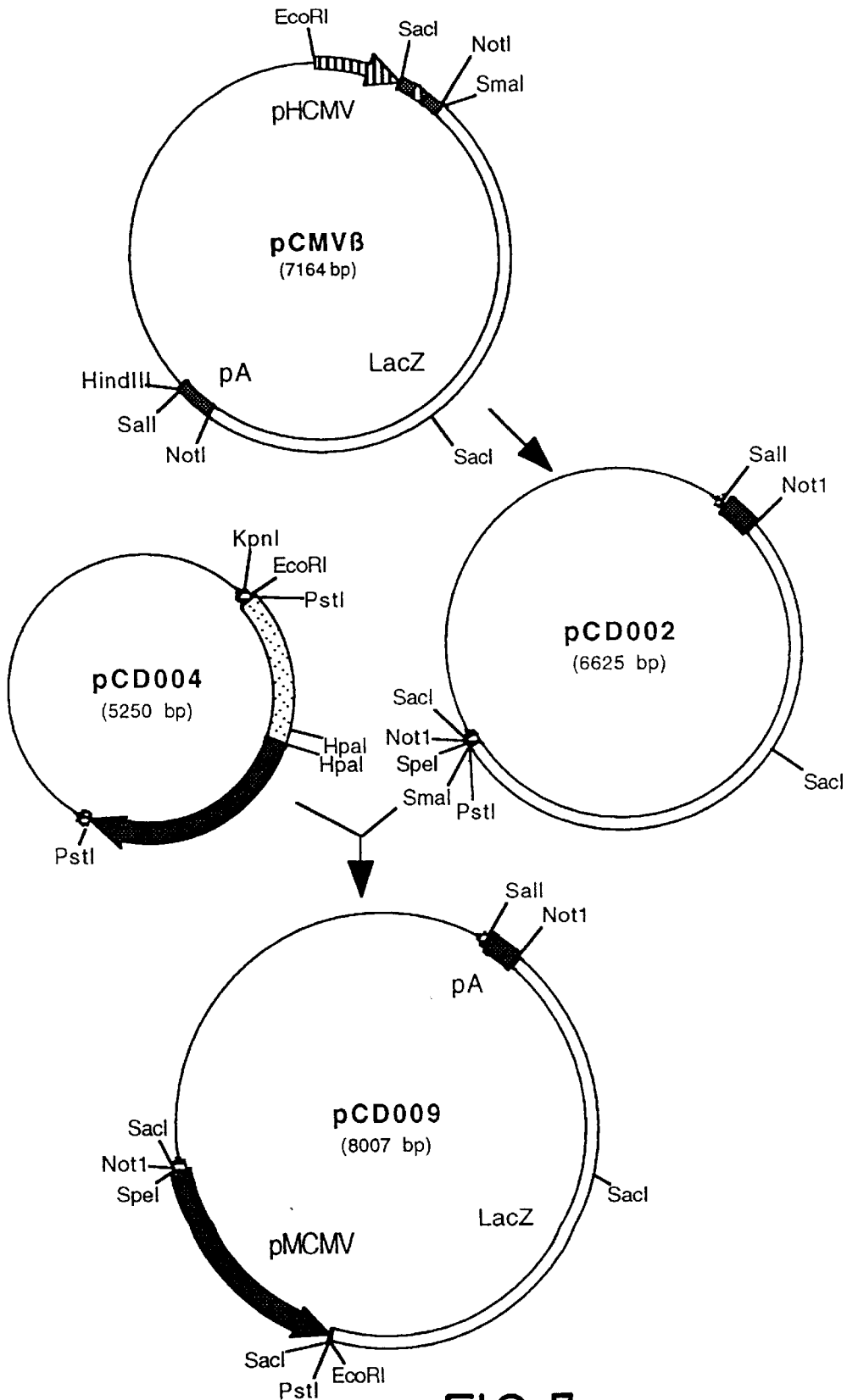

Construction of the donor plasmid pEL159 for the insertion of a cassette for the expression of the IBDV VP2 gene under the control of the MCMV IE promoter into the intergenic site between ORFs B an C, and isolation of vILTV9:

7.1—Construction of pEL070 containing a cassette for the expression of the IBDV VP2 gene under the control of the MCMV (mouse cytomegalovirus) immediate early (IE) promoter Plasmid pCMVβ (Clontech Cat # 6177-1, FIG. 7) was digested with SalI and SmaI to isolate the 3679-bp SalI-SmaI fragment containing the lacZ gene as well as the polyadenylation signal of the SV40 virus late gene. This fragment was inserted into the vector pBS-SK+ previously digested with SalI and EcoRV to give the plasmid pCD002 of 6625 bp (FIG. 7). This plasmid contains the lacZ reporter gene, but no promoter is located upstream of this gene.

MCMV virus strain Smith was obtained from the American Type Culture Collection, Rockville, Md., USA (ATCC No. VR-194). This virus was cultured on Balb/C mouse embryo cells and the viral DNA of this virus was prepared as described by Ebeling A. et al. (J. Virol. 1983. 47. 421–433). This viral genomic DNA was digested with PstI to isolate the 2285-bp PstI—PstI fragment. This fragment was cloned into the vector pBS-SK+ previously digested with PstI and treated with alkaline phosphatase to give the plasmid pCD004 (FIG. 7). Plasmid pCD004 was digested with HpaI and PstI to isolate the 1389-bp HpaI-PstI fragment which contains the promoter/enhancer region of the murine cytomegalovirus (murine cytomegalovirus=MCMV) immediate early gene (Dorsch-Häsler K. et al. Proc. Natl. Acad. Sci. 1985. 82. 8325–8329 and Patent Application WO-A-87/03905. This fragment was cloned into plasmid pCD002 previously digested with PstI and SmaI to give plasmid pCD009 or 8007 bp (FIG. 7).

A double-stranded oligonucleotide was obtained by hybridization of the following two oligonucleotides:

MB070 (SEQ ID NO:6) 5' CGAATTCACTAGTGTGT-GTCTGCAGGCGGCCGCGTGTGTGTC-GACGGTAC 3'

MB071 (SEQ ID NO:7) 5' CGTCGACACACACGCG-GCCGCCTGCAGACACACTAGTGAAT-TCGAGCT 3'

Figure 8:
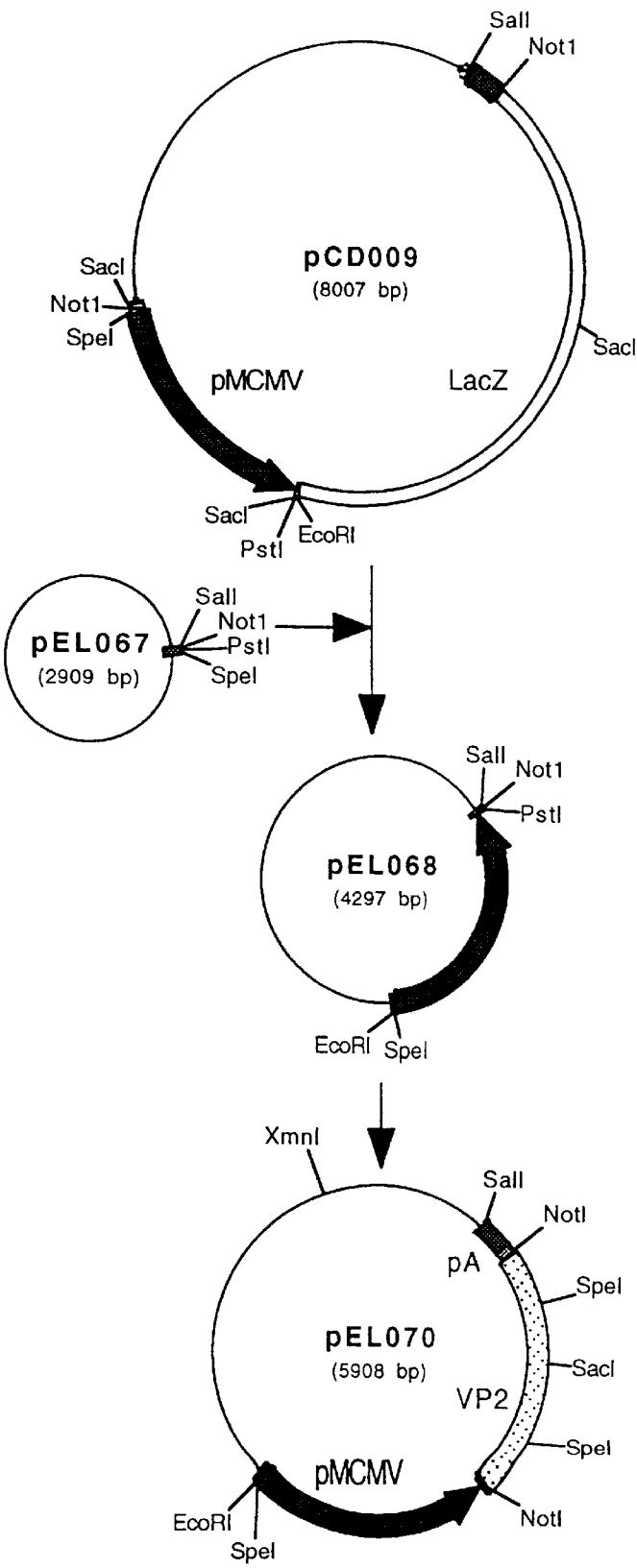

This double-stranded oligonucleotide was ligated with the vector pBS-SK+ previously digested with KpnI and SacI to give the plasmid pEL067 (FIG. 8).

Plasmid pCD009 was digested with PstI and SpeI to isolate the 1396-bp PstI-SpeI fragment. This fragment was ligated with plasmid pEL067 previously digested with PstI and SpeI to give the plasmid pEL068 of 4297 bp (FIG. 8). Plasmid pEL024 (see Example 6, Section 6.1 and FIG. 5) was digested with HindIII and NotI to isolate the 1390-bp HindIII-NotI fragment (fragment A). Plasmid pEL027 (see Example 6, Section 6.1 FIG. 5) was digested with HindIII and SalI to isolate the 235-bp HindIII-SalI fragment (fragment B). The fragments A and B were ligated together with plasmid pEL068 previously digested with NotI and SalI to give plasmid pEL070 of 5908 bp (FIG. 8). This plasmid hence contains an expression cassette consisting of the MCMV IE promoter, the VP2 gene and the polyA signal of SV40).

7.2—Construction of the donor plasmid pEL159

Figure 9:
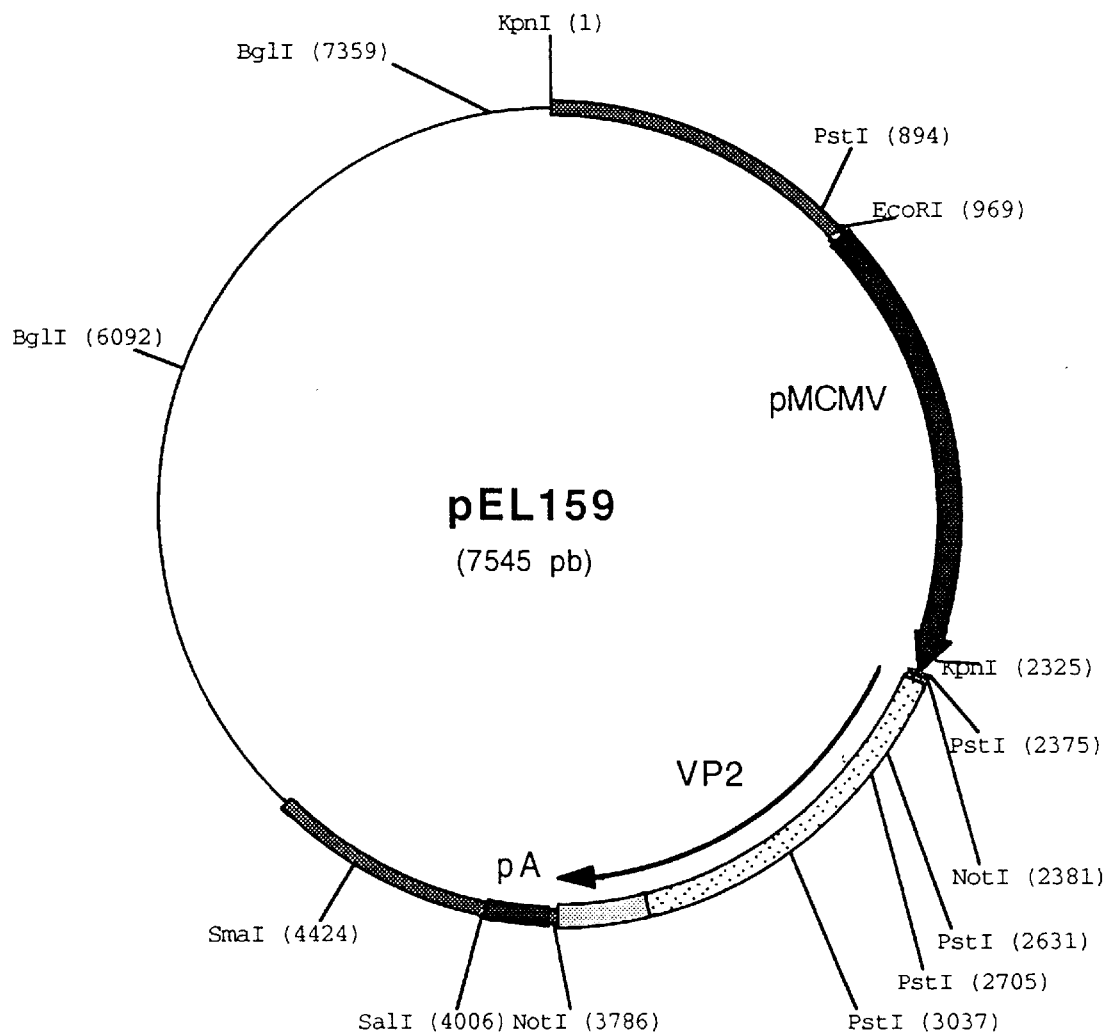

Plasmid pEL070 was digested with EcoRI, SalI and XmnI to isolate the 3035-bp EcoRI and SalI fragment. This fragment was ligated into plasmid pEL157 (see Example 5 and FIG. 3) previously digested with EcoRI and SalI to give plasmid pEL159 of 7545 bp (FIG. 9). This plasmid permits the insertion of the MCMV IE/IBDV-VP2 expression cassette into the intergenic site between ORFs B and C of the ILTV virus.

7.3—Isolation and purification of the recombinant virus vILTV9

The virus vILTV9 was isolated and purified after cotransfection of plasmid pEL159 DNA previously linearized with the enzyme BglI and the viral DNA, as described in Example 3. This recombinant contains an MCMV-IE/IBDV VP2 cassette in the intergenic site between ORFs B and C of the ILTV virus (see Example 5).

Example 8

Construction of the donor plasmid pEL160 for the insertion of a cassette for the expression of the NDV HN gene into the intergenic site between ORFs B and C, and isolation of vILTV10:

8.1—Cloning of the Newcastle disease virus (NDV) HN gene

The building of a complementary DNA library for the genome of the Newcastle disease virus (NDV), strain Texas, was carried out as described by Taylor J. et al. (J. Virol. 1990. 64. 1441–1450). A pBR322 clone containing the end of the fusion gene (F), the whole of the haemagglutinin-neuraminidase (HN) gene and the beginning of the polymerase gene was identified as pHN01. The sequence of the NDV HN gene contained in this clone is presented in FIG. 10 (SEQ ID NO:8). The plasmid pHN01 was digested with SphI and XbaI to isolate the 2520-bp SphI-XbaI fragment. This fragment was ligated with the vector pUC19 previously digested with SphI and XbaI to give the plasmid pHN02 of 5192 bp. Plasmid pHN02 was digested with ClaI and PstI to isolate the 700-bp ClaI-PstI fragment (fragment A). A PCR was carried out with the following oligonucleotides:

EL071 (SEQ ID NO:9) 5' CAGACCAAGCTTCT-TAAATCCC 3'

Figure 11:
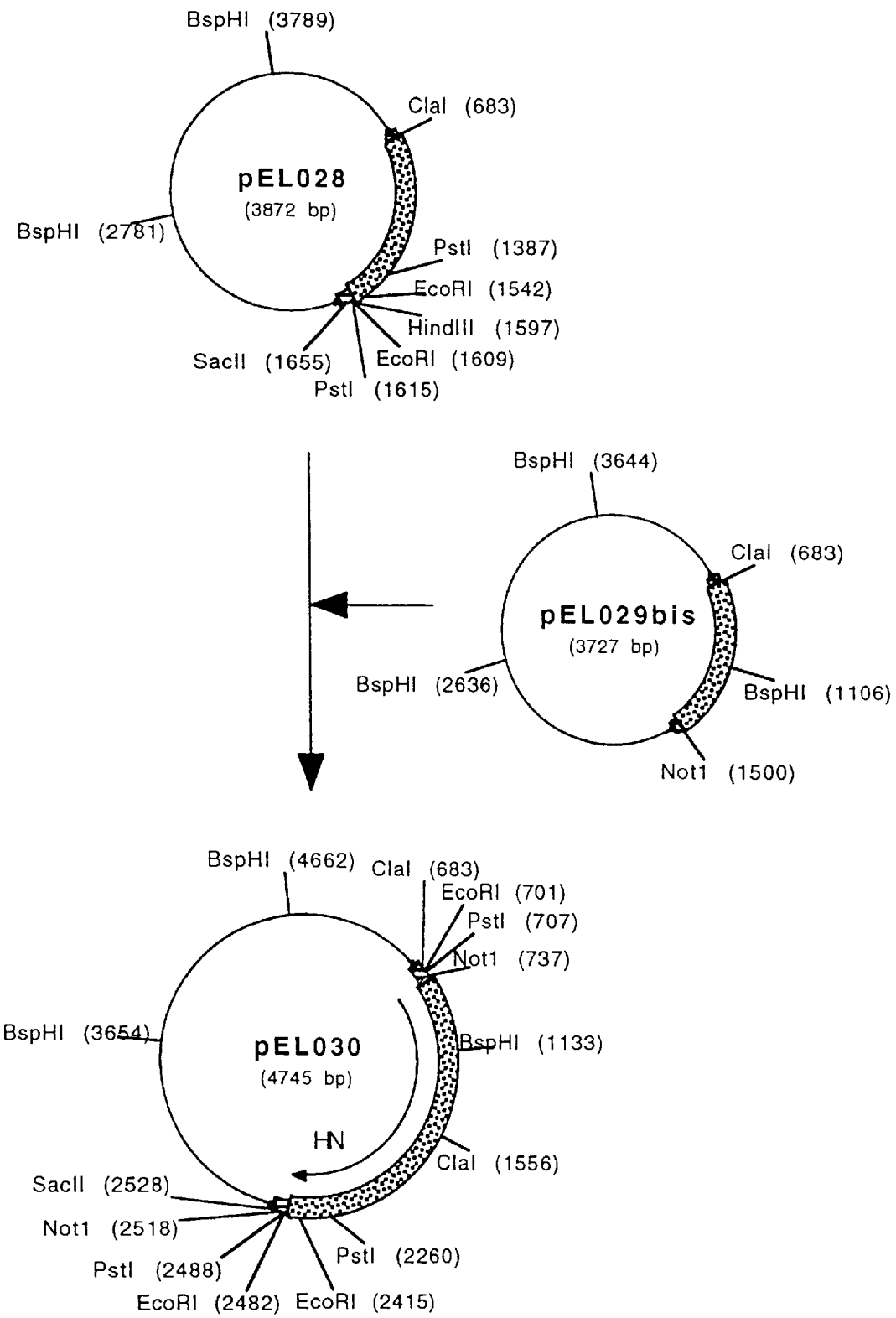

EL073 (SEQ ID NO:10) 5' GTATTCGGGACAATGC 3' and the pHN02 template to produce a PCR fragment of 270 bp. This fragment was digested with HindIII and PstI to isolate a 220-bp HindIII-PstI fragment (fragment B). The fragments A and B were ligated together with the vector pBS-SK+ previously digested with ClaI and HindIII to give the plasmid pEL028 of 3872 bp (FIG. 11). Plasmid pHN02 was digested with BsphI and ClaI to isolate the 425-bp BsphI-ClaI fragment (fragment C). A PCR was carried out with the following oligonucleotides:

EL074 (SEQ ID NO:11) 5' GTGACATCACTAGCGT-CATCC 3'

EL075 (SEQ ID NO:12) 5' CCGCATCATCAGCGGC-CGCGATCGGTCATGGACAGT 3' an the pHN02 template to produce a PCR fragment of 465 bp. This fragment was digested with BsphI and NotI to isolate the 390 bp BsphI-NotI fragment (fragment D). The fragments C and D were ligated together with the vector pBS-SK+ previously digested with ClaI and NotI to give the plasmid pEL029bis of 3727 bp (FIG. 11). Plasmid pEL028 was digested with ClaI and SacII to isolate the 960-bp ClaI-SacII fragment (fragment E). Plasmid pEL029-bis was digested with ClaI an NotI to isolate the 820-bp ClaI-NotI fragment (fragment F). The fragments E and F were listed together with the vector pBS-SK+ previously digested with NotI and SacII to give plasmid pEL030 of 4745 bp (FIG. 11).

Figure 12:
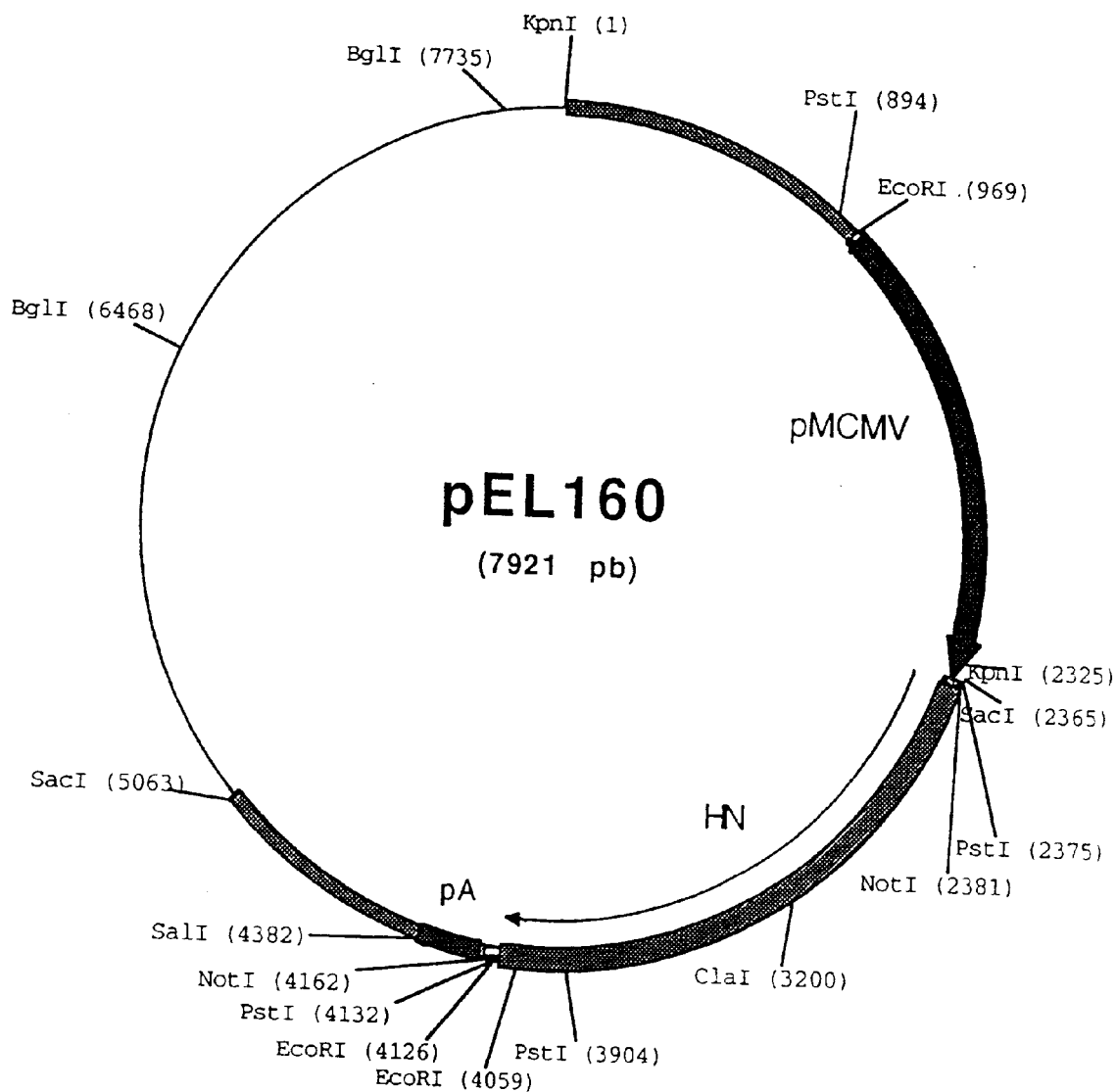

8.2—Construction of plasmid pEL160 containing a cassette for the expression of NDV HN in the intergenic site between ORFs B and C Plasmid pEL030 was digested with NotI to isolate the 1780 bp NotI—NotI fragment (complete NDV HN gene). This fragment was inserted into the NotI sites of plasmid pEL159 (Example 7, FIG. 9) in place of the 1405-bp NotI—NotI fragment containing the gene coding for the protein VP2 of IBDV; this cloning enables plasmid pEL160 of 7921 bp (FIG. 12) to be isolated. This plasmid permits the insertion of the MCMV-IE/NDV-HN expression cassette into the intergenic site between ORFs B and C of the ILTV virus.

8.3-13 Isolation and purification of the recombinant virus vILTV10

The virus vILTV10 was isolated and purified after cotransfection of plasmid pEL160 DNA previously linearized with the enzyme BglI and the viral DNA, as described in Example 3. This recombinant contains an MCMV-IE/NDV HN cassette in the intergenic site between ORFs B and C of the ILTV virus (see Example 5).

Example 9

Construction of the donor plasmid pEL161 for the insertion of a cassette for the expression of the NDV F gene into the intergenic site between ORFs B and C, and isolation of vILTV11:

9.1—Cloning of the Newcastle disease virus (NDV) F gene

A clone originating from the complementary DNA library for the Newcastle disease virus genome (see Example 8, Section 8.1) and containing the fusion gene (F) in its entirety was referred to as pNDV81. This plasmid has been described previously and the sequence of the NDV F gene present in this clone has been published (Taylor J. et al. J. Virol., 1990, 64. 1141–1450). Plasmid pNDV81 was digested with NarI and PstI to isolate the 1870-bp NarI-PstI fragment (fragment A). A PCR was carried out with the following oligonucleotides:

EL076 (SEQ ID NO:13) 5' TGACCCTGTCTGGGATGA 3'

Figure 13:
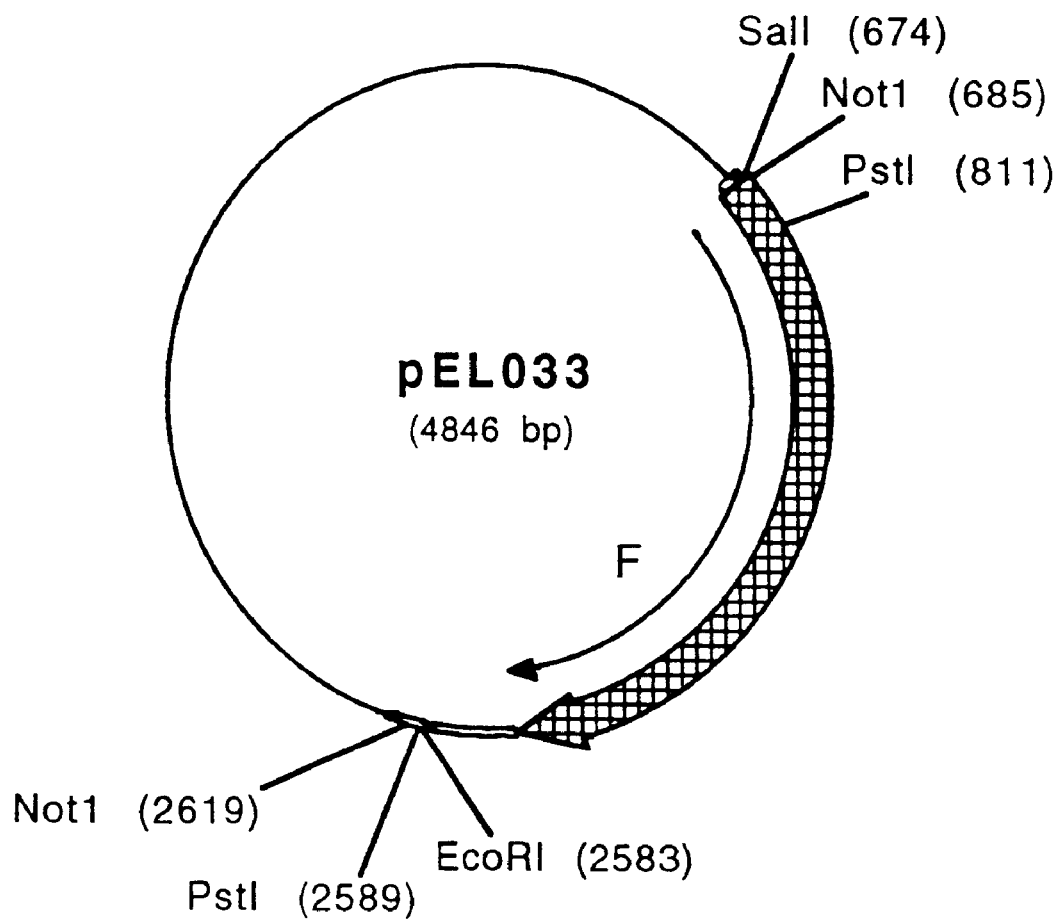

EL077 (SEQ ID NO:14) 5' GGATCCCGGTCGACA-CATTGCGGCCGCAAGATGGGC 3' and the pNDV81 template to produce a 160-bp fragment. This fragment was digested with PstI and SalI to isolate the 130-bp PstI-SalI fragment (fragment B). The fragments A and B were ligated together with the vector pBS-SK+ previously digested with CalI and SalI to give plasmid pEL033 of 4846 bp (FIG. 13).

Figure 14:
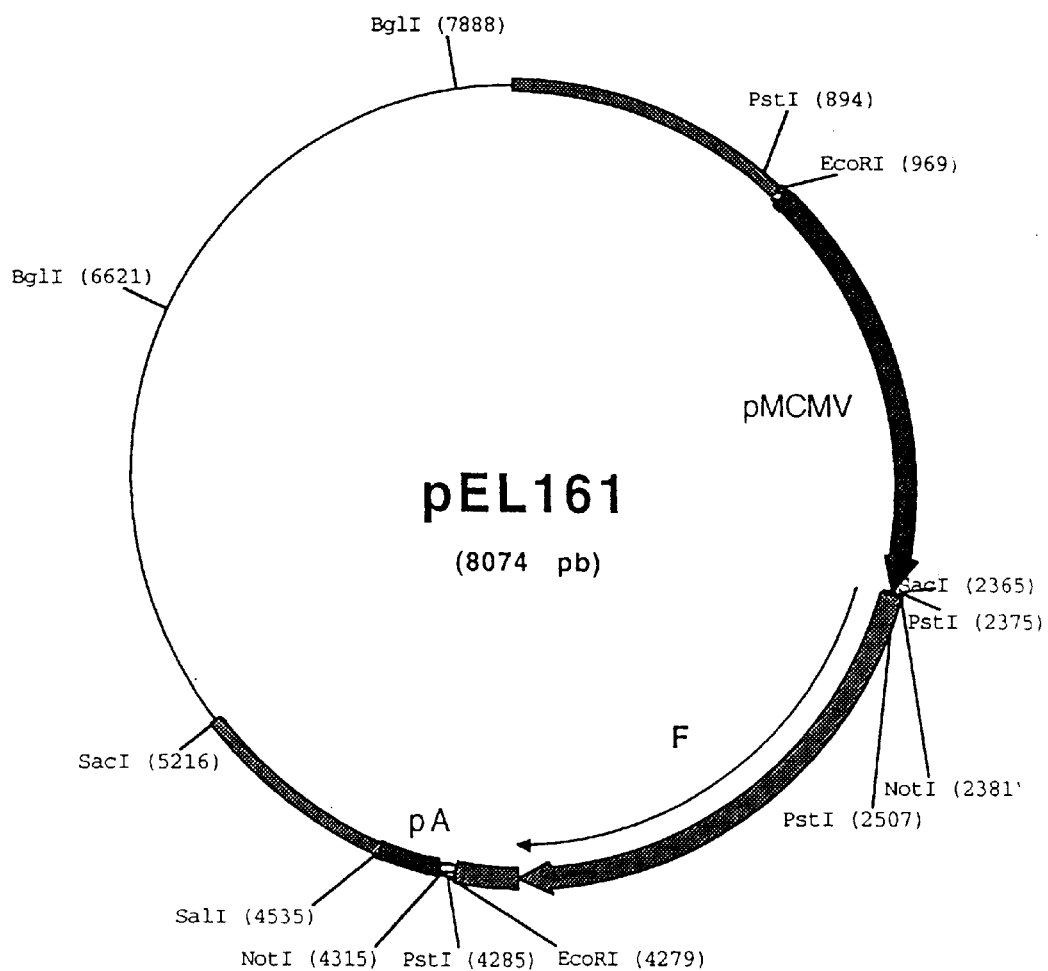

9.2—Construction of plasmid pEL161 containing a cassette for the expression of the NDV F gene in the intergenic site between ORFs B and C Plasmid pEL033 was digested with NotI to isolate the 1935-bp NotI—NotI fragment (complete F gene). This fragment was inserted into the NotI sites of plasmid pEL159 (Example 7, FIG. 9) in place of the 1405-bp NotI—NotI fragment containing the gene coding for the protein VP2 of IBDV; this cloning enabled plasmid pEL161 of 8074 bp (FIG. 14) to be isolated. This plasmid permits the insertion of the MCMV-IE/NDV-F expression cassette into the intergenic site between ORFs B and C of the ILTV virus.

9.3—Isolation and purification of the recombinant virus vILTV11

The virus vILTV11 was isolated and purified after cotransfection of plasmid pEL161 DNA previously linearized with the enzyme BglI and the viral DNA, as described in Example 3. This recombinant contains an MCMV-IE/ NDV F cassette in the intergenic site between ORFs B and C of the ILTV virus (see Example 5).

Example 10

Figure 15:
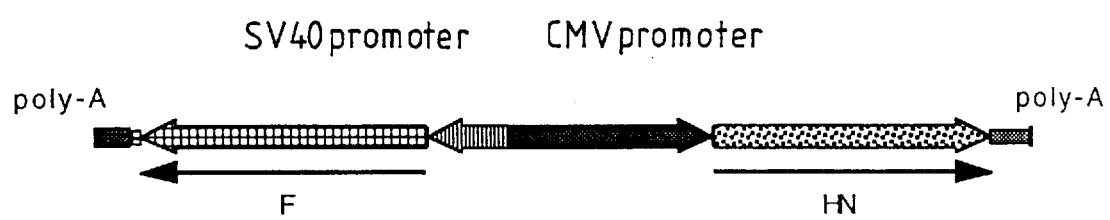

Construction of a donor plasmid for the insertion of a double cassette for the expression of the NDV HN and F genes into the intergenic site between ORFs B and C, and isolation of a recombinant ILTV virus:

A double cassette for the expression of two genes, for example the NDV HN and F genes, can be constructed. Such a construction is outlined in FIG. 15. In this construction, the 5' end of the two promoters are adjacent so the transcription of the two genes takes place in opposite directions. One of the two promoters is the MCMV IE promoter and the other promoter (referred to allied promoter) is the SV40 promoter (present in the plasmid pSVbeta, Clontech Laboratories, Palo Alto, Calif. 94303-4607, USA). In this arrangement, the allied promoter is activated by the enhancer region of the CMV IE promoter.

Figure 3:
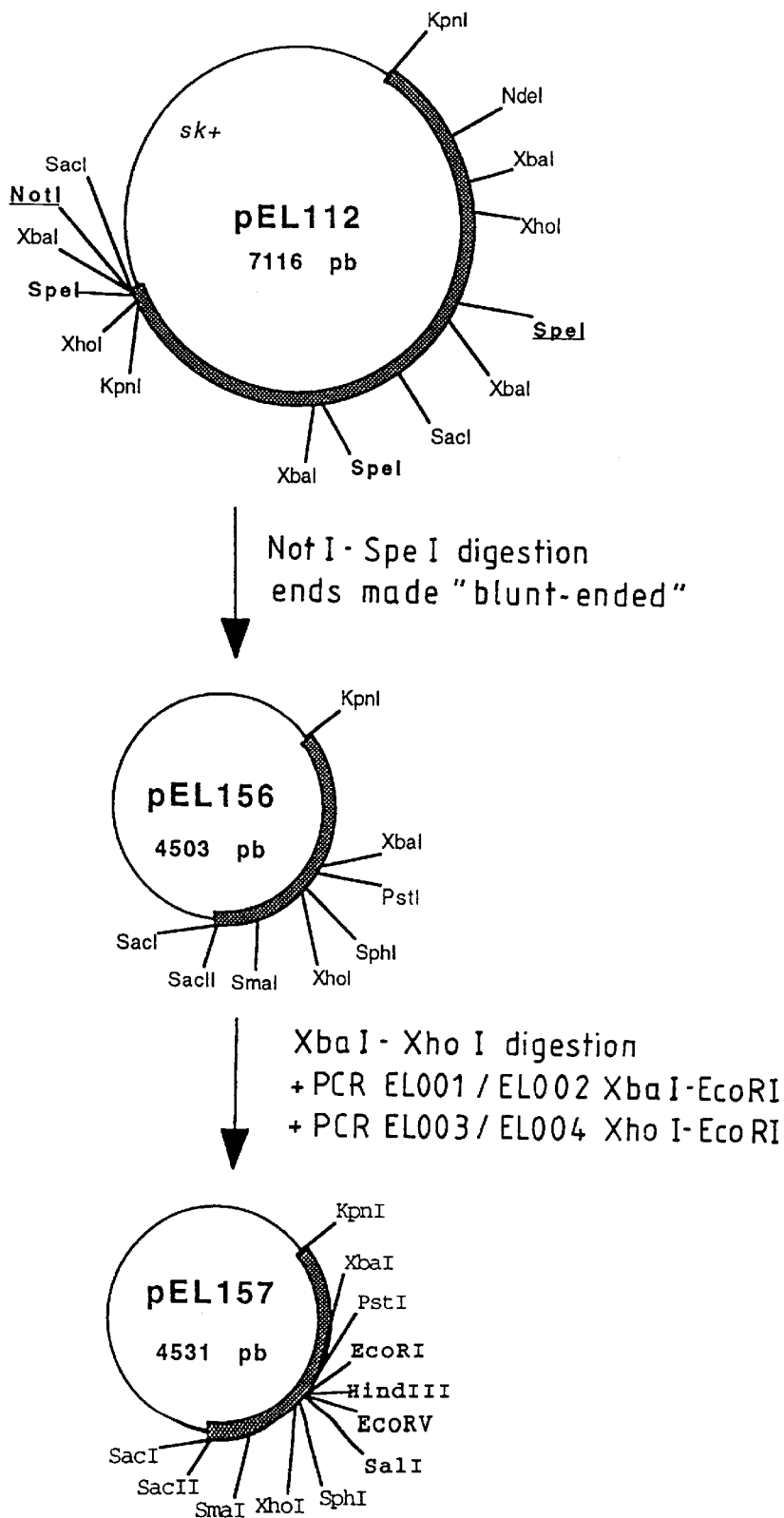

This double expression cassette may then be inserted into the donor plasmid described above (pEL157 described in Example 5 and shown in FIG. 3).

The isolation of the recombinant viruses takes place in the same manner as above (see Example 3).

Example 11

Construction of the donor plasmid pEL163 for the insertion of a cassette for the expression of the MDV gB gene into the intergenic site between ORFs B and C, and isolation of vILTV12:

11.1—Cloning of the gB gene of the Marek's disease virus

Figure 16:
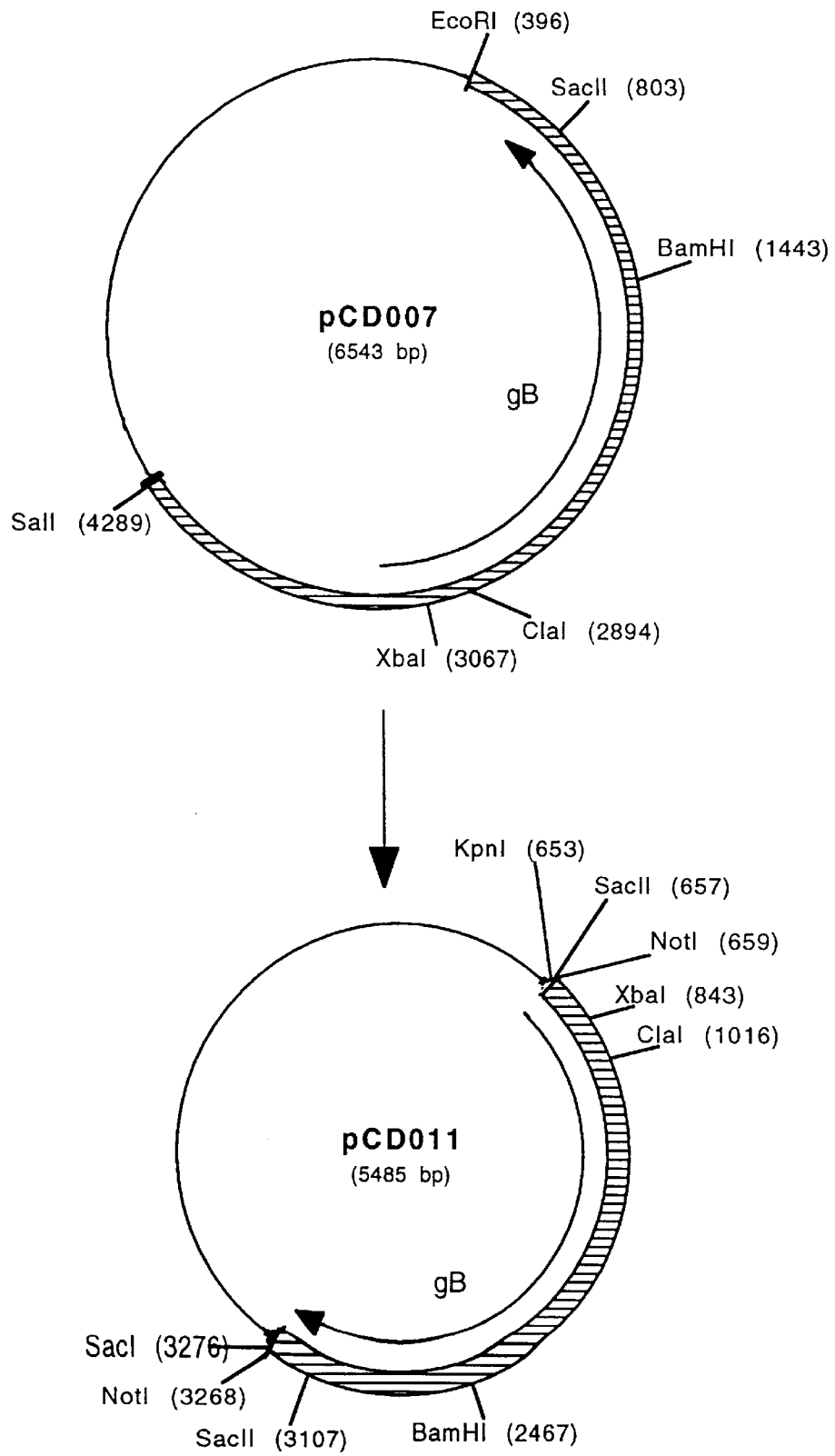

The 3.9-kbp EcoRI-SalI fragment of the genomic DNA of the MDV virus strain RB1B containing the MDV gB gene (sequence published by Ross N. et al. J. Gen. Virol. 1989. 70, 1789–1804) was ligated with the vector pUC13 previously digested with EcoRI and SalI to give the plasmid pCD007 of 6543 bp (FIG. 16). This plasmid was digested with SacI and XbaI to isolate the 2260-bp SacI-XbaI fragment (central part of the gB gene=fragment A). A PCR was carried out with the following oligonucleotides:

CD001 (D δ Q ID NO:15) 5' GACTGGTACCGCGGC-CGCATGCACTTTTTAGGCGGAATTG 3'

CD002 (SEQ ID NO:16) 5' TTCGGGACATTTTCGCGG 3' and the pCD007 template to produce a PCR fragment of 222 bp. This fragment was digested with KpnI and XbaI to isolate a 190-bp KnpI-XbaI fragment (5' end of the gB gene=fragment B). Another PCR was carried out with the following oligonucleotides:

CD003 (SEQ ID NO:17) 5' TATATGGCGTTAGTCTCC 3'

CD004 (SEQ ID NO:18) 5' TTGCGAGCTCGCGGC-CGCTTATTACACAGCATCATCTTCTG 3' and the pCD007 template to produce a PCR fragment of 195 bp. This fragment was digested with SacI and SacII to isolate the 162-bp SacI-SacII fragment (3' end of the gB gene= fragment C). The fragments A, B and C were ligated together with the vector pBS-SK+ previously digested with KpnI and SacI to give plasmid pCD011 of 5485 bp (FIG. 16).

11.2—Construction of plasmid pEL163 containing a cassette for the expression of the MDV gB gene in the intergenic site between ORFs B and C of the ILTV virus.

Figure 17:
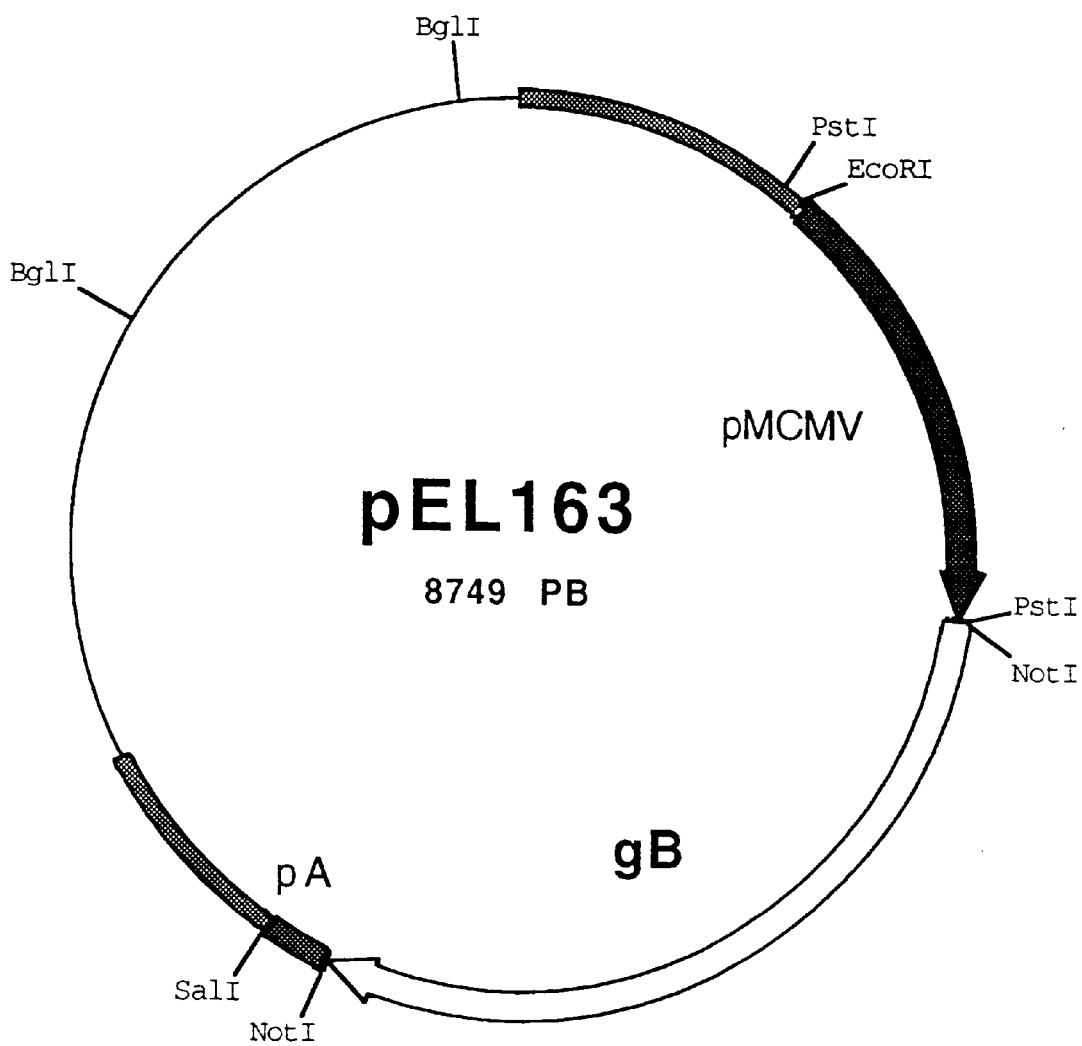

Plasmid pCD011 was digested with NotI to isolate the 2608-bp NotI—NotI fragment (complete MDV gB gene). This fragment was inserted into the NotI sites of plasmid pEL159 (Example 7, FIG. 9) in place of the 1405-bp NotI—NotI fragment containing the gene coding for the protein VP2 of IBDV; this cloning enabled plasmid pEL163 of 8749 bp (FIG. 17) to be isolated. This plasmid permits the insertion of the MCMV-IE/MDV-gB expression cassette into the intergenic site between ORFs B and C of the ILTV virus.

11.3—Isolation and purification of the recombinant virus vILTV12

The virus vILTV12 was isolated and purified after cotransfection of plasmid pEL161 DNA previously linearized with the enzyme BglI and the viral DNA, as described in Example 3. This recombinant contains an MCMV-IE/ MDV gB cassette in the intergenic site between ORFs B and C of the ILTV virus (see Example 5).

Example 12

Construction of a donor plasmid for the insertion of a cassette for the expression of IBV gene(s) into the intergenic site between ORFs B and C, and isolation of recombinant ILTV virus:

According to the same strategy as that described above for the insertion of single cassettes (Examples 6, 7, 8, 9 and 11) or for the insertion of double cassettes (Example 10) into the site described above (Example 5), it is possible to produce recombinant ILTV viruses expressing at a high level the membrane (M) or spike (S), or part of spike (S1 or S2) or nucleocapsid (N) proteins of the avian infectious bronchitis virus (IBV). In particular, a double expression cassette is produced with the S gene under the control of the CMV IE promoter and the M gene under the control of the allied promoter.

Example 13

Construction of donor plasmids for the insertion of cassettes for the expression of gene(s) of other avian pathogenic agents or of immunomodulatory peptide in the site described, and isolation of recombinant ILTV viruses:

According to the same strategy as that described above the insertion of single cassettes (Examples 6, 7, 8, 9 and 11) or for the insertion of double cassettes (Example 10) into the site described above (Example 5), it is possible to produce recombinant ILTV viruses expressing at a high level immunogens of CAV (and in particular a double cassette for the expression of the genes coding for VP1 and VP2), of the chicken pneumovirosis virus or of other avian pathogenic agents, or alternatively immunomodulatory peptides, and in particular cytokines.

Example 14

Production of vaccines:

The recombinant viruses obtained according to the invention are produced on embryonated eggs. The harvested viral solution is then diluted in a stabilizing solution for lyophilization, distributed on the basis of 1000 vaccinal does per vial and lastly lyophilized.

We claim:

1. An ILTV virus comprising at least one heterologous nucleotide sequence inserted into the insertion locus formed by the intergenic region located between the stop codons of ORF B and ORF C of ILTV, which region, in a particular strain of ILTV, is defined between nucleotides 908 and 994 in SEQ ID NO:1.

2. The ILTV virus of claim 1 wherein the at least one nucleotide sequence is inserted by simple insertion or after total or partial deletion of the insertion locus.

3. The ILTV virus claim 1 including a strong eukaryotic promoter for expression of the at least one nucleotide sequence.

4. The ILTV virus of claim 3 wherein the strong promoter is selected from the group consisting of: a CMV immediate early promoter, Rous sarcoma virus (RSV) LTR promoter, and SV40 virus early promoter.

5. The ILTV virus of claim 4 wherein the CMV immediate early promoter is selected from the group consisting of the murine and the human CMV immediate early promoter.

6. The ILTV virus of claim 1 comprising at least two nucleotide sequences inserted into the insertion locus under the control of different eukaryotic promoters.

7. The ILTV virus of claim 6 wherein the eukaryotic promoters are CMV immediate early promoters of different animal origin.

8. The ILTV virus of claim 6 comprising a first nucleotide sequence under the control of a first promoter and a second nucleotide sequence under the control of a second promoter, wherein the promoters are in the opposite orientation leading to transcription in opposite directions.

9. The ILTV virus of claim 8 wherein the first promoter is the CMV immediate early promoter.

10. The ILTV virus of claim 1 comprising an expression cassette inserted into the insertion locus, wherein the expression cassette comprises a promoter, two or more genes separated pairwise by an IRES, and a polyadenylation signal.

11. The ILTV virus of claim 1 comprising a nucleotide sequence encoding an antigenic polypeptide of an avian pathogen inserted into the insertion locus.

12. The ILTV virus of claim 11 wherein the nucleotide sequence encodes an antigenic polypeptide of Newcastle disease virus (NDV), the Gumboro disease virus (IBDV), the Marek's disease virus (MDV), the infectious bronchitis virus (IBV), the chicken anaemia virus (CAV), or the chicken pneumovirosis virus.

13. The ILTV virus of claim 12 wherein the nucleotide sequence codes for NDV F or HN antigens.

14. The ILTV virus of claim 12 wherein the nucleotide sequence codes for MDV gB, gC, gD or gH+gL antigens.

15. The ILTV virus of claim 12 wherein the nucleotide sequence codes for at least one antigen selected from the group consisting of: IBDV VP2 antigen, IBV S, or part of S, M, and N antigens, CAV VP1 and VP2 antigens, and the chicken pneumonovirosis virus G and F antigens.

16. The ILTV virus of claim 1 comprising a nucleotide sequence coding for an immunomodulatory polypeptide inserted into the insertion locus.

17. The ILTV virus of claim 16 wherein the immunomodulatory polypeptide is a cytokine.

18. An immunological composition comprising the ILTV virus of any one of claims 1–17.

19. An immunological composition comprising as a mixture, or to be mixed, at least two ILTV viruses of any one of claims 1–17, wherein the ILTV viruses are comprised of different inserted sequences.

20. A method for expressing at least one heterologous nucleotide sequence comprising contacting the ILTV virus of any one of claims 1–17 with a suitable cell under conditions for expression of the heterologous nucleotide sequence.

21. Recombinant live avian vaccine comprising as vector an ILTV virus comprising and expressing at least one heterologous nucleotide sequence, this nucleotide sequence being inserted into the insertion locus formed by the intergenic region located between the stop codons of ORF B and ORF C of ILTV, which region, in a particular strain of ILTV, is defined between nucleotides 908 and 994 in SEQ ID NO:1.

22. Recombinant live vaccine according to claim 21, characterized in that the nucleotide sequence or sequences is/are inserted by simple insertion or after total or partial deletion of the insertion locus.

23. Recombinant live vaccine according to claim 21, characterized in that, to express the inserted nucleotide sequence, the vector comprises a strong eukaryotic promoter.

24. Recombinant live vaccine according to claim 23, characterized in that the strong promoter is selected from the group consisting of: CMV immediate early promoter, Rous sarcoma virus (RSV) LTR promoter and SV40 virus early promoter.

25. The recombinant live vaccine according to claim 24 wherein the CMV immediate early promoter is the murine or human CMV immediate early promoter.

26. Recombinant live vaccine according to claim 21, characterized in that it comprises at least two nucleotide sequences inserted into the insertion locus under the control of different eukaryotic promoters.

27. Recombinant live vaccine according to claim 26, characterized in that the eukaryotic promoters are CMV immediate early promoters of different animal origins.

28. Recombinant live vaccine according to claim 26, characterized in that it comprises a first nucleotide sequence under the control of a first promoter and and a second nucleotide sequence under the control of a second promoter, wherein the promoters are in the opposite orientation leading to transcription in opposite directions.

29. The recombinant live vaccine of claim 28 wherein the first promoter is the CMV immediate early promoter.

30. Recombinant live vaccine according to claim 21, characterized in that it comprises, inserted into the insertion locus, an expression cassette comprising in succession a promoter, two or more genes separated pairwise by an IRES, and a polyadenylation signal.

31. Recombinant live vaccine according to claim 21, characterized in that it comprises a nucleotide sequence coding for an antigenic polypeptide of an avian pathogenic agent, this sequence being inserted into the insertion locus.

32. Recombinant live vaccine according to claim 31, characterized in that it comprises a sequence coding for an antigen of an avian pathogenic agent selected from the group consisting of the Newcastle disease virus (NDV), the Gumboro disease virus (IBDV), the Marek's disease virus (MDV), the infectious bronchitis virus (IBV), the chicken anaemia virus (CAV) and the chicken pneumovirosis virus.

33. Recombinant live vaccine according to claim 32, characterized in that it comprises a nucleotide sequence selected from the nucleotide sequences coding for the polypeptides F and HN of the NDV virus.

34. Recombinant live vaccine according to claim 32, characterized in that it comprises a nucleotide sequence selected from the nucleotide sequences coding for the polypeptides gB, gC, gD and gH+gL of the MDV virus.

35. Recombinant live vaccine according to claim 32, characterized in that it comprises at least one nucleotide sequence selected from the group of sequences corresponding to the VP2 antigens of IBDV, to the S, or part of S, M and N antigens of the IBV virus, to the VP1 and VP2 antigens of CAV and to the G and F antigens of the chicken pneumovirosis virus.

36. Recombinant live vaccine according to claim 21, characterized in that it comprises a nucleotide sequence coding for an immunomodulatory polypeptide, this sequence being inserted into the insertion locus.

37. Recombinant live vaccine according to claim 36, characterized in that this nucleotide sequence is selected from the group of sequences coding for cytokines.

38. Multivalent vaccine formula comprising, as a mixture or to be mixed, at least two recombinant live vaccines as defined in claim 21, these vaccines comprising different inserted sequences.

* * * * *